United States Patent [19]

Morita

[11] Patent Number: 5,755,733
[45] Date of Patent: May 26, 1998

[54] LANCET ASSEMBLY

[75] Inventor: Susumu Morita, Nishinomiya, Japan

[73] Assignee: APLS Co., Ltd., Osaka, Japan

[21] Appl. No.: 682,706

[22] PCT Filed: Nov. 27, 1995

[86] PCT No.: PCT/JP95/02401

§ 371 Date: Jul. 29, 1996

§ 102(e) Date: Jul. 29, 1996

[87] PCT Pub. No.: WO96/16599

PCT Pub. Date: Jun. 6, 1996

[30] Foreign Application Priority Data

Nov. 29, 1994 [JP] Japan .................................. 6-294793

[51] Int. Cl.⁶ .................................................... A61B 17/32
[52] U.S. Cl. ............................................................ 606/182
[58] Field of Search ..................................... 606/181–185; 128/770–771

[56] References Cited

U.S. PATENT DOCUMENTS

| | | |
|---|---|---|
| Re. 32,922 | 5/1989 | Levin et al. . |
| 3,030,959 | 4/1962 | Grünert . |
| 3,358,689 | 12/1967 | Higgins . |
| 4,375,815 | 3/1983 | Burns . |
| 4,379,456 | 4/1983 | Cornell et al. . |
| 4,388,925 | 6/1983 | Burns . |
| 4,414,975 | 11/1983 | Ryder et al. . |
| 4,416,279 | 11/1983 | Lindner et al. . |
| 4,442,836 | 4/1984 | Meinecke et al. . |
| 4,449,529 | 5/1984 | Burns et al. . |
| 4,452,243 | 6/1984 | Leopoldi et al. . |
| 4,462,405 | 7/1984 | Ehrlich . |
| 4,469,110 | 9/1984 | Slama . |
| 4,503,856 | 3/1985 | Cornell et al. . |
| 4,514,609 | 4/1985 | Fricke et al. . |
| 4,517,978 | 5/1985 | Levin et al. . |
| 4,527,561 | 7/1985 | Burns . |
| 4,535,769 | 8/1985 | Burns . |
| 4,539,988 | 9/1985 | Shirley et al. . |
| 4,545,376 | 10/1985 | Beiter . |
| 4,553,541 | 11/1985 | Burns . |
| 4,577,630 | 3/1986 | Nitzsche et al. . |
| 4,580,564 | 4/1986 | Andersen . |
| 4,580,565 | 4/1986 | Cornell et al. . |
| 4,610,667 | 9/1986 | Pedicano et al. . |
| 4,616,649 | 10/1986 | Burns . |
| 4,624,253 | 11/1986 | Burns . |
| 4,648,408 | 3/1987 | Hutcheson et al. . |
| 4,653,513 | 3/1987 | Dombrowski . |
| 4,658,821 | 4/1987 | Chiodo et al. . |
| 4,676,244 | 6/1987 | Enstrom . |
| 4,677,979 | 7/1987 | Burns . |

(List continued on next page.)

FOREIGN PATENT DOCUMENTS

| | | |
|---|---|---|
| MR 0933 1992 | 10/1992 | Denmark . |
| 0 403 873 A1 | 12/1990 | European Pat. Off. . |
| 0 589 186 A1 | 3/1994 | European Pat. Off. . |
| 0 613 656 A2 | 9/1994 | European Pat. Off. . |
| 0 633 004 A1 | 1/1995 | European Pat. Off. . |
| 92 05 278 | 6/1992 | Germany . |

OTHER PUBLICATIONS

Lagana, "Guide to Finger–Pricking Equipment," *Diabetese Self–Management* (R.A. Rapaport Publishing Inc.) 7, 6–11 (Jul./Aug. 1990).

Modulohm A/S Catalog (1992).

*Primary Examiner*—William Lewis
*Attorney, Agent, or Firm*—Leydig, Voit & Mayer, Ltd.

[57] ABSTRACT

There is provided a blade type lancet assembly of which sterile condition is readily to be kept.

A lancet assembly is composed of a lancet structure and a holder which is combined with the lancet structure, the lancet structure includes a lancet member having a pricking member and an ejector which ejects the lancet member, and an exposed portion of the pricking member is covered with a resin.

25 Claims, 25 Drawing Sheets

U.S. PATENT DOCUMENTS

| | | |
|---|---|---|
| 4,712,548 | 12/1987 | Enstrom . |
| 4,715,374 | 12/1987 | Maggio . |
| 4,735,203 | 4/1988 | Ryder et al. . |
| 4,738,261 | 4/1988 | Enstrom . |
| 4,794,926 | 1/1989 | Munsch et al. . |
| 4,817,603 | 4/1989 | Turner et al. . |
| 4,844,095 | 7/1989 | Chiodo et al. . |
| 4,856,515 | 8/1989 | Turner et al. . |
| 4,858,607 | 8/1989 | Jordan et al. . |
| 4,869,249 | 9/1989 | Crossman et al. . |
| 4,889,117 | 12/1989 | Stevens . |
| 4,892,097 | 1/1990 | Ranalletta et al. . |
| 4,924,879 | 5/1990 | O'Brien . |
| 4,976,724 | 12/1990 | Nieto et al. . |
| 4,990,154 | 2/1991 | Brown et al. . |
| 4,994,068 | 2/1991 | Hufnagle . |
| 4,995,402 | 2/1991 | Smith et al. . |
| 5,026,388 | 6/1991 | IngaLz . |
| 5,047,044 | 9/1991 | Smith et al. . |
| 5,074,872 | 12/1991 | Brown et al. . |
| 5,100,427 | 3/1992 | Crossman et al. . |
| 5,105,823 | 4/1992 | Blum . |
| 5,133,730 | 7/1992 | Biro et al. . |
| 5,147,375 | 9/1992 | Sullivan et al. . |
| 5,207,699 | 5/1993 | Coe . |
| 5,314,442 | 5/1994 | Morita . |
| 5,356,420 | 10/1994 | Czernecki et al. . |
| 5,366,469 | 11/1994 | Steg et al. . |
| 5,366,470 | 11/1994 | Ramel . |
| 5,397,334 | 3/1995 | Schenk et al. . |
| 5,439,473 | 8/1995 | Jorgensen . |
| 5,487,748 | 1/1996 | Marshall et al. ............ 606/182 |
| 5,514,152 | 5/1996 | Smith ............ 606/182 |
| 5,527,334 | 6/1996 | Kanner et al. ............ 128/770 |
| 5,554,166 | 9/1996 | Lange et al. ............ 128/770 |

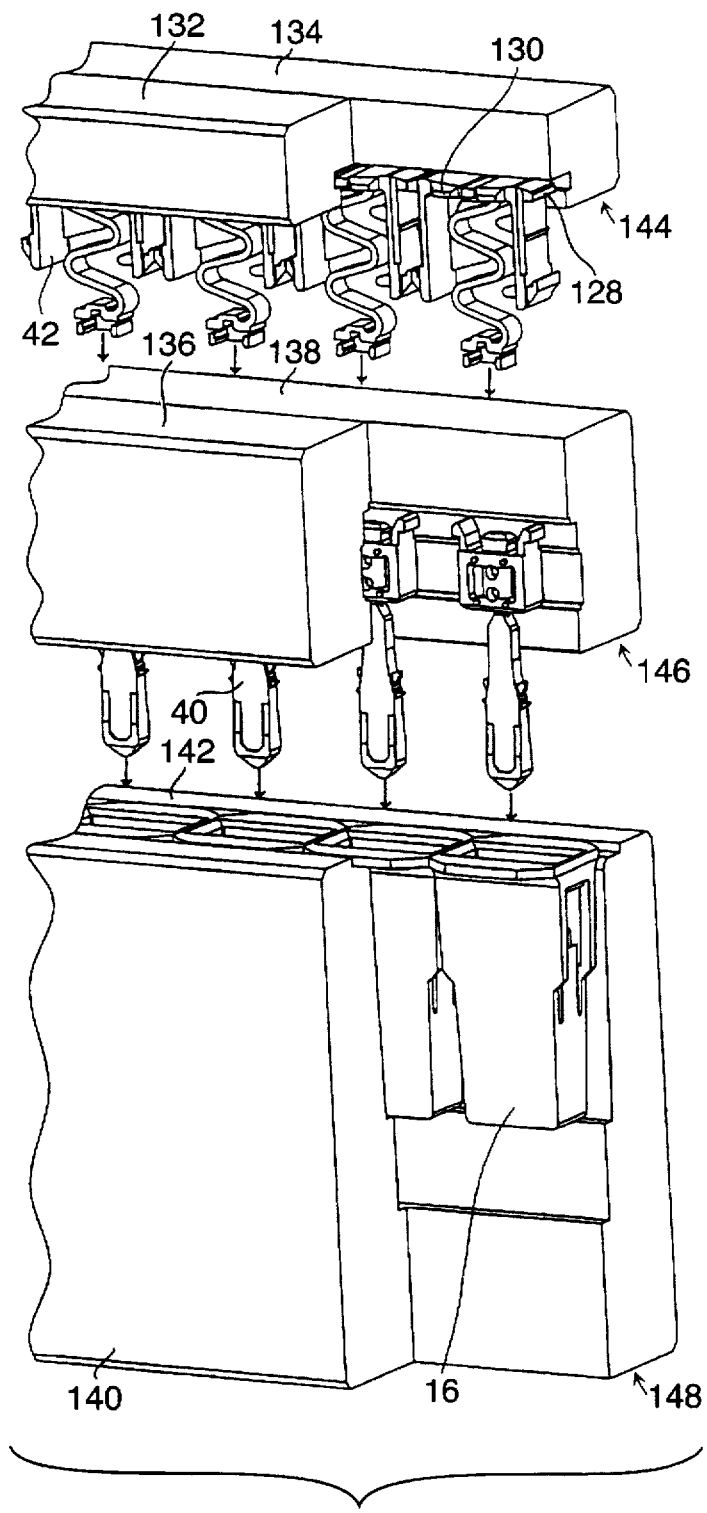 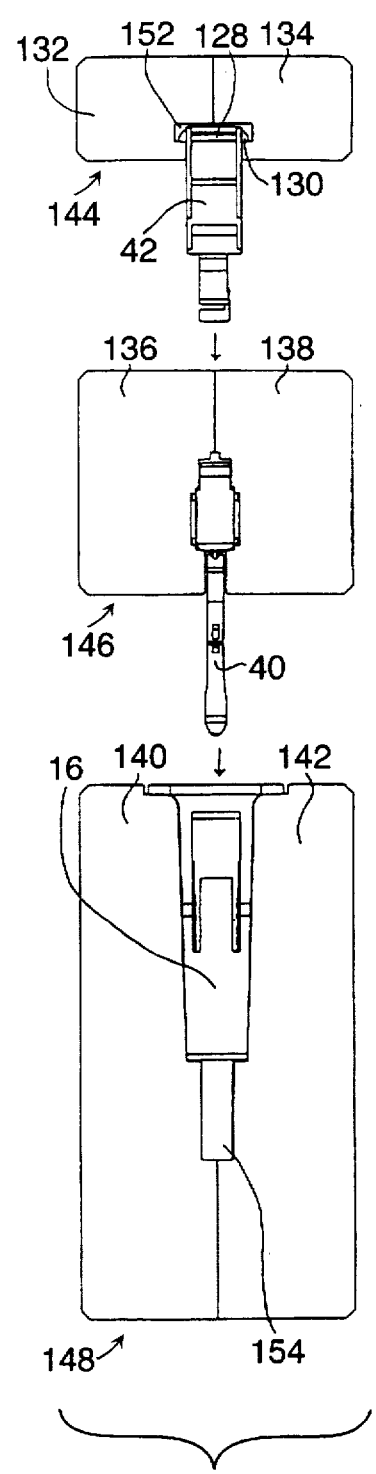
FIG. 27A   FIG. 27B

5,755,733

LANCET ASSEMBLY

FIELD OF THE INVENTION

The present invention relates generally to a lancet assembly or a pricking device such as a finger pricking device which wounds skin to permit the collection of a small amount of blood. More specifically, the invention is directed to such an assembly which easily ensures sterility of the lancet before its use, which is also disposable which is easily produced and which is conveniently used.

BACKGROUND OF THE INVENTION

Various lancet assemblies or finger-pricking devices are commercially available to hospitals, clinics, doctors' offices, and the like, as well as to individual consumers. Such devices include a lancet body which comprises a sharp-pointed member or a sharp-edged member, namely a pricking member (such as a blade-like member or a needle-like member) that is used to make a quick puncture or incision of the patient's skin in order to provide a small outflow of blood. Various tests may be employed using only small amounts of blood so that blood flowing from such a wound or puncture is normally sufficient for these tests.

Such lancet assemblies are typically sterilized beforehand when they are produced, and they have to be maintained in a sterile condition before use to ensure that the lancet is not contaminated by its surrounding environment. In addition, in order to prevent the lancet from wounding a user of the assembly or any other object around the user upon contact of the pricking member therewith during handing the assembly, the pricking member generally should not be unnecessarily exposed.

After using of the assembly, sufficient care must be taken by the user to avoid being punctured by a used lancet assembly. The risks in handling used lancets are greatly increased due to present day concerns regarding communicable diseases transmitted through body fluids such as blood. The lancet assembly must be carefully handled until it is properly disposed. Advances have been made in recent years to increase safety in handling such used devices. For example, pricking devices are currently available which include a single shot firing mechanism having the features of automatic ejection and retraction of the blade edge tip from and into the assembly.

One such lancet assembly, for example, is shown in Danish Design Patent No. MR 0933 (granted on Oct. 1, 1992) or its counterpart U.S. Pat. No. 5,439,473. The Danish Design Patent lancet assembly is a self-contained device that includes a lancet structure, which includes a unitary ejector (projector or injector) and lancet element, used in combination with a holder (or a protective sheath or sleeve). The lancet structure is contained in the holder after use. The disclosures of the Danish Design Patent and the U.S. Patent are incorporated herein with the reference for all purposes.

The Danish Design Patent lancet assembly is commercially available from Modulohm A/S (Denmark) under a trade name of Vitrex, of which structure and a working principles are schematically shown in FIGS. 1 to 7, wherein FIG. 1 shows a lancet assembly 10 before its use wherein a lancet structure 14 is incorporated into a holder 16;

FIG. 2 schematically shows a schematic front view of the lancet assembly in FIG. 1 wherein only the holder 16 is shown in a cross-sectional view so as to clarify a condition of the lancet structure 14 in the holder 16;

FIG. 3 schematically shows a schematic front view which is similar to the view shown in FIG. 2 wherein the lancet structure 14 is further depressed into inside of the holder 16 from the condition shown in FIG. 2;

FIG. 4 schematically shows a schematic front view which is similar to the view shown in FIG. 2 wherein the lancet structure 14 is being ejected for its use;

FIG. 5 schematically shows a schematic front view which is similar to the view shown in FIG. 2 showing the lancet structure 14 after use;

FIG. 6 schematically shows an exploded perspective view of the lancet structure 14 which is used for the lancet assembly shown in FIGS. 1 to 5 before a blade 44 has been mounted; and FIG. 7 schematically shows a perspective view of the lancet structure 14 after the blade 44 has been inserted from a condition shown in FIG. 6.

The shown lancet assembly 10 essentially comprises a unitary lancet structure 14 and a holder 16. It is preferable that the lancet structure 14 of the lancet assembly 10, excluding the pricking member 44 (for example a blade member), be made of a polymer, such as a polyacetal (POM) resin, a polybutylene terephalate (PBT) resin or a polyester copolymer resin for the member 14, and the holder 16 be made of an acrylonitrile-butadiene-styrene (ABS) resin, a polycarbonate resin, a polystyrene resin, a polyethylene resin or a polypropylene resin, each being injection molded as a unitary structure. During use, the members 14 and 16 move between the relative positions shown in FIGS. 2, 3, 4 and 5 sequentially.

The holder 16 includes a cavity 18 extending along an ejecting direction of the lancet structure 14 which cavity cooperates with an opening 20 for receiving the unitary lancet structure 14. Adjacent the opening 20 are outwardly extending flanges 21, as shown in FIG. 1, which are used to hold the holder 16 between the fingers of the user during operation of the lancet assembly 10. The cavity 18 includes guidance channels 80 on and along opposite sides of the inner wall of the cavity 18, which channels cooperate with mating protrusions 50 (such as pins) provided on a lancet body 46 of the lancet structure 14 so as to smoothly control movement of the lancet body 46 along the channels 80 within the cavity 18. The opposite end (a side wall) of the holder 16 relative to the opening 20 is provided with an aperture 26 through which, during use of the assembly 10, a tip portion of the pricking member 44 protrudes and then retracts.

The holder 16 further includes channels or openings 30 along opposite sides, which open into the cavity 18 (and thus the channels pass through the walls of the holder). For further controlling movement of the unitary lancet structure 14 within the holder 16, arms 32 of the holder 16 disposed within the openings 30 include engaging protrusions 34, which extend into the cavity 18. The significance of these members will become clear upon a more detailed explanation of the unitary lancet structure 14, which will be shown below.

The unitary lancet structure 14 comprises a lancet member 40 and an ejector 42. The lancet member 40 includes a pricking member (such as a blade or a needle) 44 and a lancet body 46 having a pair of cantilevered arms 48. To guide movement of the lancet member 40 through the holder 16, pins 50 are provided on the remaining opposite sides (the front side and the back side in FIG. 2) of the lancet body 46. As the lancet structure 14 is positioned within the holder 16 and actuated, the pins 50 cooperate with the guidance channels 80 provided on the inner walls of the cavity 18 to control the periscoping movement of the lancet member 40 having the pricking element 44 along the channels 80 within the holder 16. The pricking element 44 of the lancet member 40, which is secured to and protrudes from one side of the lancet body 46, is formed from stainless steel or the like and includes a sharp point for piercing the patient's skin.

The ejector 42 includes a compressible spring member 54 and a U-shaped actuator 56. The U-shaped actuator 56 includes a base portion 58, to which the compressible spring member 54 is coupled, and upstanding actuator arms 60 are positioned perpendicularly at both ends thereof. The opposite end of the spring member 54 is attached to the lancet body 46. The lancet structure 14 is sized such that it may be disposed and smoothly move within the opening 20 and cavity 18 of the holder 16 in the positions shown in FIGS. 2 to 5.

To retain the lancet structure 14 in place within the opening 20 and the cavity 18 of the holder 16 prior to actuation of the lancet assembly 10, as shown in FIG. 2, outwardly extending lips (protrusions) 62 and 64 are provided along the outer surfaces of the actuator arms 60. In the position of FIG. 2, the lips 62 having tapers which opens upwardly are disposed within the channels 30 such that each of the lips 62 seats against the upper edge of each channel 30. As a result, the lancet structure 14 cannot be pulled out of the holder 16 even though it is drawn along a direction opposite to the arrow A. The lips 64 are disposed adjacent the opening 20 of the holder 16. It may be noted that the outer surfaces of the lips 64 are tapered upwardly from the opening 20 so that the U-shaped actuator 56 easily slides into the holder 16 with cooperation of a tapered portion 20 (so called guiding portion) of the wall edge forming the opening 20 when the actuator 56 is depressed into the holder 16.

Before being in the condition of FIG. 2, the lips 62 seat against the edges of the opening 20 of the holder 16 when the lancet structure 14 is inserted through the opening 20. Similarly to the lips 64, the tapers of both the lips 62 and the opening 20 make the insertion of the lancet structure 14 smooth and result in the condition shown in FIG. 2. The tapers cooperate with elasticity (a property which causes transient deformation and then return therefrom) of the actuator 56, especially the arms 60 so as to make the insertion of the lancet structure 14 into the holder 16 smooth.

The lips 64 further function to lock the lancet structure 14 in position within the holder 16 (a position wherein the pricking element 44 does not come out of the holder 16) after use of the lancet assembly 10. Namely, as seen from FIG. 5 which shows a position after use, the lips 64 are disposed within the respective channels 30 such that they may abut against the upper edges of the channels 30 as stops when the lancet structure 14 is pulled along a direction of the arrow A' so as to pull the structure 14 of the holder, which abutment prevents the members 14 and 16 from separating from each other, namely the lancet structure 14 is not pulled out of the holder 16.

The actuator arms 60 function as an actuator for releasing (or ejecting) the lancet member 40 to permit the blade end 44 to protrude from the aperture 26, as will be apparent from the explanation set forth below. The end of each actuator arm 60 is provided with an inwardly tapered lip 68 along the inner surface of the arm 60, and an outwardly tapered lip 62 having an outside surface 70.

The operation of the lancet assembly 10 will be described with reference to FIGS. 2–5. Prior to actuation of the assembly, the members 14 and 16 of the assembly 10 are disposed in the relative positions shown in FIG. 2. The lancet assembly is usually supplied to the user in the form shown in FIG. 2. To use the assembly, the user takes the holder 16 between his fingers and places the end of the holder 16 containing the aperture 26 against the skin of the patient. The user then uses his thumb to depress the U-shaped actuator 56 into the holder 16 along a direction of the arrow A, as shown in FIG. 2. As the actuator 56 is depressed, the engaging protrusions 34 of the holder 16 contact extensions 48 on the arms 48 cantilevered at ends of the lancet body 46 (provided that a clearance is originally present between them) so that the arms 48 cannot further proceed and the lancet member 40 is held in this position. As a result of the lancet member 40 being held in this position, the protrusions 34 compress and energize the spring member 54 as the user continues to depress the actuator 56. In the embodiment shown in FIG. 2, since the arms 48 have already substantially abutted against the protrusions 34, energizing starts simultaneously with the depression.

As the user further continues to depress the actuator 56, the ends of the actuator arms 60 approach and contact or almost contact the engaging protrusions 34, move the ends of the arms 32 outwardly and the ends of the arms 48 inwardly with aid of the tapered surfaces 70 and lips 68 and then separate (or release) the extensions 48 of the cantilevered arms 48 of the lancet member 40 from the engaging protrusions 34 of the holder 16 which has been engaged with the arms 48, as shown in FIG. 3. This is because easy transient deformation (or displacement) of the arms 32, 60 and 48, especially the ends thereof due to the plasticity resulted from plastic materials which form the holder 16 (including the arms 32), the actuator 56 and the lancet body 46 (including the arms 48).

As the engaging protrusions 34 and the arms 48 disengage from the abutting position thereof, the compressed spring member 54 is substantially no longer restrained along a direction of the arrow A, and releases the accumulated energy to eject the lancet member 40 toward the aperture 26, as shown in FIG. 4. The compressed spring 54 extends such that the lancet member 40 moves to a position as shown in phantom in FIG. 4, so that the pricking member 44 protrudes from the aperture 26 to pierce the skin. After extension, the spring member 54 returns to its position immediately due to its plasticity, as shown in FIG. 5.

After the use of the lancet assembly 10, it is the position shown in FIG. 5. Since the pricking element 44 is held in the holder 16 and the lips 64 function as stops, the lancet structure 14 is not pulled out of the holder 16 even when the lancet structure is pulled along a direction of the arrow A', as described above. So, the pricking element is not exposed outside and the used lancet assembly can be handled and disposed safely. In addition, even when such an assembly is intended to be reused, it is impossible to do so since the spring member cannot be energized.

DISCLOSURE OF THE INVENTION

In the prior art lancet assembly using the blade as described above, the pricking member 44 is not shielded and it is exposed. Namely, the blade edge 44 of the lancet structure 14 incorporated into the holder 16 is not covered at all and it is exposed within the holder 16. Therefore, each individual lancet assembly in the position as shown in FIG. 1 must be packed as a unit in a blister package or a resin made container, the whole of which has to then be sterilized. This type of packaging and its sterilization are relatively expensive (the cost for the sterilization is proportional to a volume including the package).

As shown in FIG. 6, the lancet structure 14 is assembled by inserting the exposed blade 44 in the direction of the arrow into the lancet body 46. FIG. 7 shows the position of the blade 44 and lancet structure 14 after the insertion. In order to assemble the lancet assembly 10, the lancet structure 14 is inserted into the holder 16 while the blade 44 is exposed as in FIG. 7. Therefore, a step is required in which the blade 44 is exposed during handling (for example, a step in which the blade 44 is inserted to form the lancet structure 14 or a step in which the lancet structure 14 having the inserted blade 44 is inserted into the holder 16). In any such a step, since the blade 44 is exposed, its tip is likely to contact other object so that the edge tip will very likely be damaged or otherwise injure said other object. Further, the blade 44 is very likely to be contaminated with microorganisms such as a bacteria.

Other objects of the present invention will be clarified according to explanations set forth below.

It is an object of the present invention to overcome the problems just described above, and other problems which will be understood from the following description of the present invention and preferred embodiments thereof.

In order to achieve the above and other objects, according to a first aspect of the present invention, there is provided a lancet assembly as described above characterized in that a pricking member of a lancet structure is covered with a resin so that the pricking member of the assembly is not exposed prior to its use. Namely, the lancet assembly according to the present invention comprises a holder and a lancet structure. The lancet structure comprises a lancet member having a pricking member and an ejector which ejects the lancet member. The pricking member is characterized in that a portion which is to be exposed from the lancet member if the absence of the resin is shielded with a resin shield.

In the first embodiment of the first aspect, the lancet member is characterized in that it comprises a shielded pricking member in which the pricking member is covered with the resin, and a lancet body, and the ejector, the lancet body and the shielded pricking member are substantially integrally bonded.

In the second embodiment of the first aspect, the lancet member is characterized in that it comprises a shielded pricking member in which the pricking member is covered with the resin, and a lancet body, the lancet body is substantially integrally bonded to the ejector, and the lancet body and the shielded pricking member are separated from each other and have portions which mate together to form tight engagement with each other.

In the third embodiment of the first aspect, the lancet member is characterized in that it comprises a shielded pricking member in which the pricking member is covered with the resin, and a lancet body, the lancet body is substantially integrally bonded to the shielded pricking device, and the lancet body and the ejector are separated from each other and have portions which mate together to form tight engagement with each other.

In the fourth embodiment of the first aspect, the lancet member is characterized in that it comprises a shielded pricking member in which the shielded member is covered with the resin, and a lancet body, the lancet body and the shielded pricking member are separated from each other and have portions which mate together to form tight engagement with each other, and the ejector and the lancet body are separated from each other and have portions which mate together to form tight engagement with each other.

In any embodiment of the present invention, it is preferable that the covering (or shielding) resin is provided with at least one notch at a position along the shielded pricking member where the resin is to be broken. This position is predetermined so that the covering resin is easily broken when it is pulled along an ejection direction of the pricking member. In this way, the pricking member is exposed with ease. This preferable embodiment of the present invention is particularly effective in an embodiment in which the pricking member is in the form of a blade.

In any embodiment of the present invention, it is preferable that the covered pricking member comprise two sets of stops along its outside surface. The stops are positioned preferably such that an aperture of a holder through which the pricking member passes is located between the two sets of the stops.

In any of the above lancet assemblies according to the present invention, the holder used therein may have a structure which is substantially the same as that of the holder (or sleeve) of the Danish Design Patent or the U.S. Patent which has been described in the "BACKGROUND OF THE INVENTION" section of this specification. Similarly, the lancet structure of the present invention may have substantially the same structure or mechanism as that of the Danish Design Patent or the U.S. Patent except the shielded pricking member and the relationship between the ejector, lancet body and the shielded pricking member.

For example, structures or mechanisms in which the lancet structure is positioned and held in various sequence positions in the holder, the lancet body is ejected, and the lancet structure is held in the holder after use (namely, an ejector mechanism in which the lancet assembly is operated including before and after use thereof) may be substantially the same as those of the Danish Design Patent or the U.S. Patent. Although there are the lips 68 on the inside surfaces and the lips 62 on the outside surfaces of the actuator arms 60, at least either the lips 68 or the lips 62 are sufficient provided that the engaged lancet body 46 can be released from the engaging protrusion 34. For example, the lips 68 may be omitted.

These features and other features of the present invention as well as effects provided by those features will be easily understood by the following description of some preferred and illustrative embodiments of the present invention and with reference to accompanying drawings.

BRIEF DESCRIPTION OF THE DRAWINGS

FIG. 27A schematically shows a perspective view which shows assembling the lancet assembly of the third embodiment according to the present invention. FIG. 27B is an end view of the assembly shown in FIG. 27A.

In those drawings, the numerals indicate the following members: 10: lancet assembly, 14: lancet structure, 16: holder, 18: cavity, 20: opening, 21: flange, 26: aperture, 30: channel, 32: arm, 34: protrusion, 40: lancet member, 42: ejector, 44: pricking member, 46: lancet body, 48: arm, 50: pin, 54: spring member, 56: actuator, 58: base portion, 60: arm, 62, 64: lip, 66: protrusion, 70: tapered surface, 80: channel, 82: covering resin, 84: covered (shielded) pricking member, 86: convex portion, 88: concave portion, 90: notch, 92: first stop, 94: second stop, 96: holder and surface, 98: tip portion of covering resin, 100: female member, 102: male member, 104,106: edge, 112: bottom portion, 120: entanglement preventive member, 122: coil spring, 124: non-slip member, 128: spacer member, 130: rib member, 132–142: assembling tool for lancet assembly, 144–148: assembling line, 150: tapered portion, and 152: channel. Throughout the drawings, corresponding members or portions have the same numeral.

PREFERRED MODES FOR CARRYING OUT THE INVENTION

Although the present invention will be described mainly with reference to the preferred embodiments, especially an embodiment in which the pricking member is in the form of the blade, the present invention is not limited to such an embodiment and applicable to the pricking member in the form of a needle, provided that no substantially adverse problem occurs.

Figure 8:
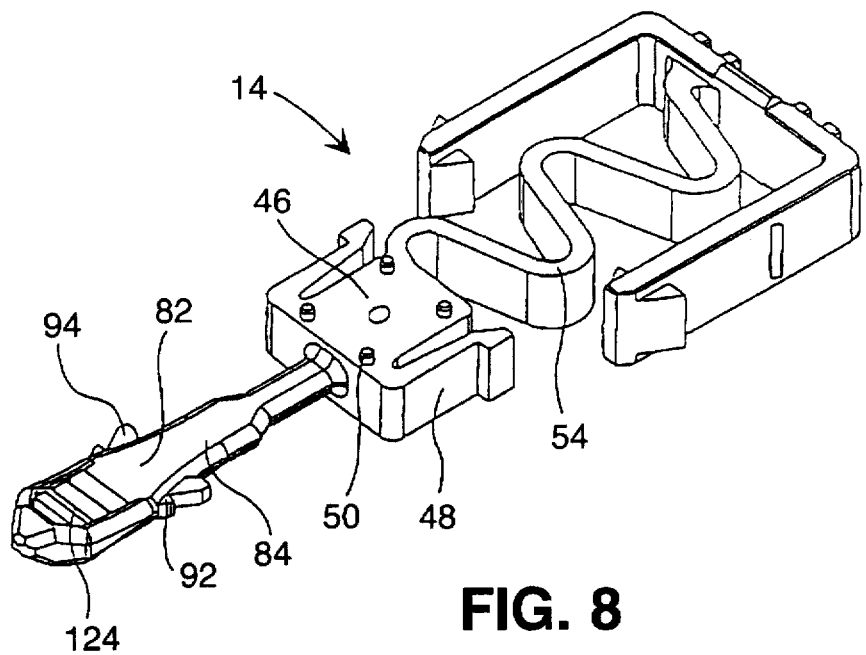
FIG. 8 schematically shows a perspective view of a lancet structure of a lancet assembly of the first embodiment of the first aspect according to the present invention.
Figure 9:
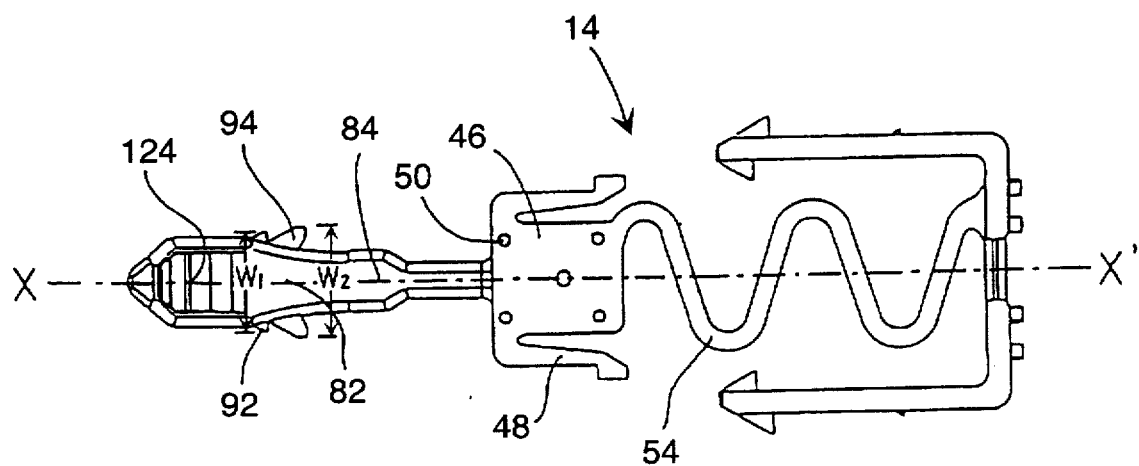
FIG. 9 schematically shows a plane view of the lancet structure shown in FIG. 8.

A lancet structure 14 of the first embodiment of the first aspect according to the present invention is shown in the perspective view of FIG. 8 and the plane view of FIG. 9. In these drawings, the pricking member 44 (for example, a blade such as that shown exposed in the prior art lancet assembly as described above) is now covered or shielded with a resin portion 82, and thus is not visible in the drawings. Other features than this covering or shield, the lancet structure 14 may be substantially the same as the lancet structure of the Danish Design Patent or the U.S. Patent which has been described in the above; the lancet structure 14 functions and effects provided by said other features are substantially the same as those provided by such a prior art lancet structure.

Figure 6:
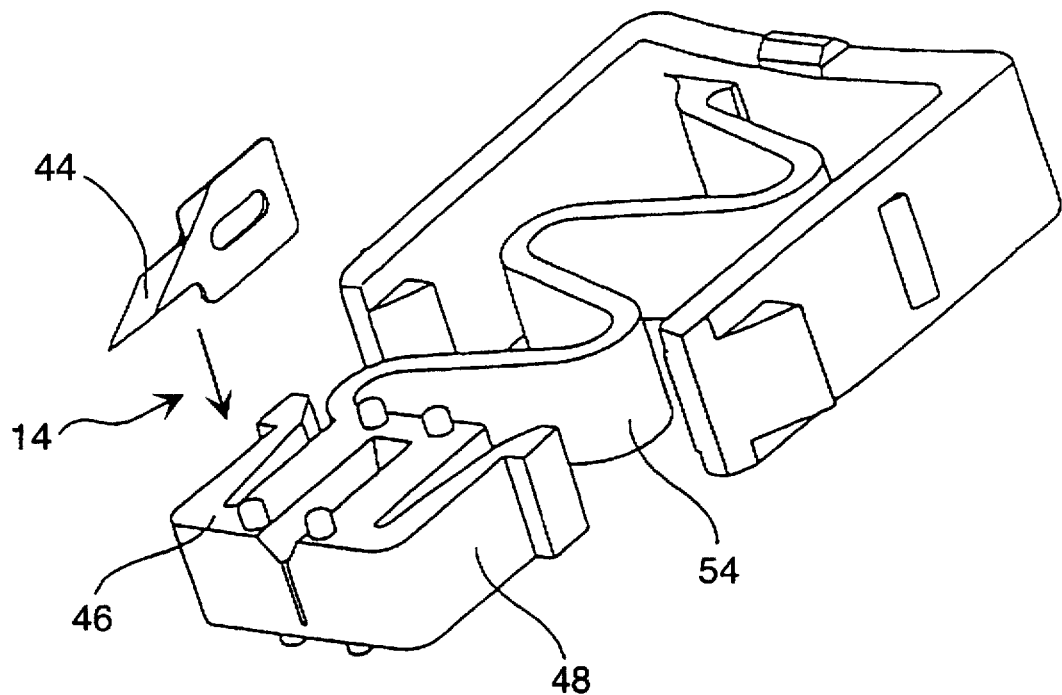
FIG. 6 schematically shows an exploded perspective view of the lancet structure 14 before a blade 44 has been mounted.
Figure 7:
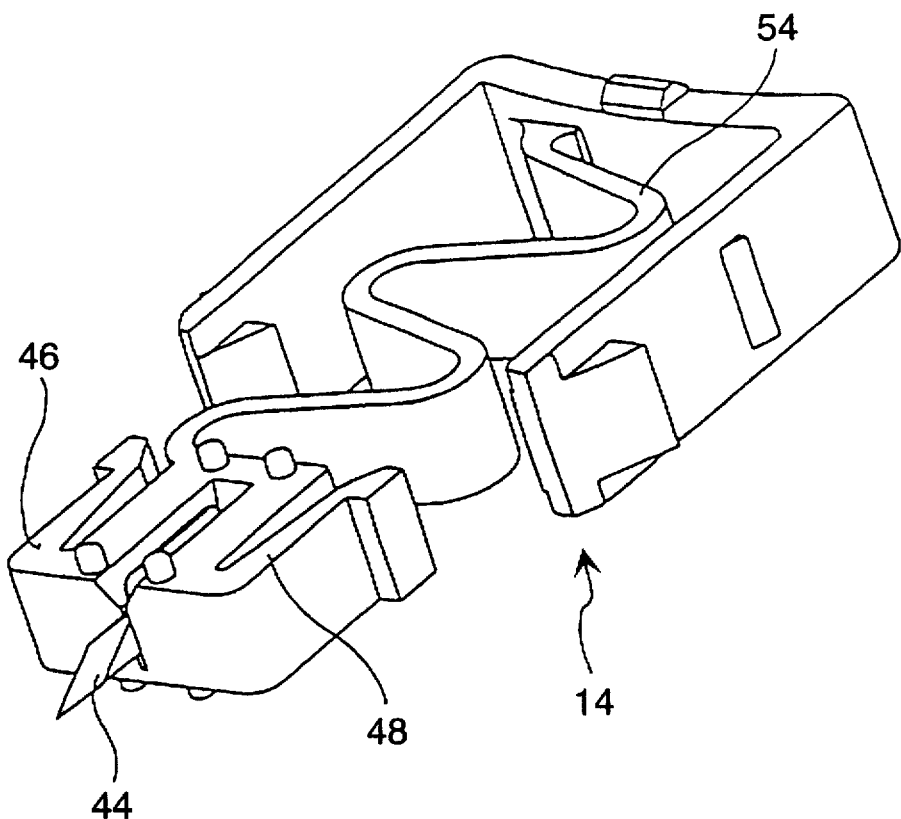
FIG. 7 schematically shows a perspective view of the lancet structure 14 of FIG. 6 after the blade 44 has been inserted.

Formation of such a resin cover 82 may be carried out in various manners and any known suitable manner may be used. For example, a lancet structure 14 can be molded as a unitary element while the blade 44 is held. Alternatively, a cover part 82 having a cavity in the form of a sheath into which the pricking member 44 can be inserted may be formed, and a lancet body structure 14 containing the blade 44 with its exposed edge portion may be separately formed beforehand as described with reference to FIGS. 6 and 7. The exposed edge portion of the blade 44 may then be inserted into the cavity of the part 82 and the part 82 may be secured to an end surface of the lancet body 46 by any suitable means such as ultrasonic welding or an adhesive to have a lancet structure 14 as shown in FIG. 8.

The resin cover 82 is preferably so formed that its tip portion protrudes from the aperture 26 of the holder 16 when the lancet structure 14 is incorporated into the holder 16 prior to use, whereby the protruding tip portion of the resin cover can be easily pulled using fingers. For example, the resin cover in the embodiment shown in FIG. 8 is of a relatively flat shape at its end portion, on which surface steps are provided as non-slip member 124. The resin cover 82 preferably has a portion along which tensile strength is weakened to such an extent that the resin cover may be removed to expose the pricking member 44 by merely pulling the tip portion of the resin cover 82. To provide such weakened tensile strength, the resin cover has a thinned section at a certain predetermined point so that the resin cover is likely to be broken at that point.

For example, the resin cover may be provided with a notch, which will be explained in detail below.

When the pricking member 44 is covered with the resin cover, the sharp tip (or edge) portion of the pricking member 44 does not contact any other object upon incorporation of the lancet structure 14 into the holder 16. As a result, the tip portion of the blade will not damage other objects and/or the tip not be damaged by other objects.

In addition, since the pricking member 44 is not exposed, only the covered pricking member structure 84, which includes the pricking member 44 requires sterilization and the cover 82 functions as a package so that individual lancet assemblies need not be packed into sterile packages, greatly reducing the costs of packing, as well as sterilizing costs.

Figure 10:
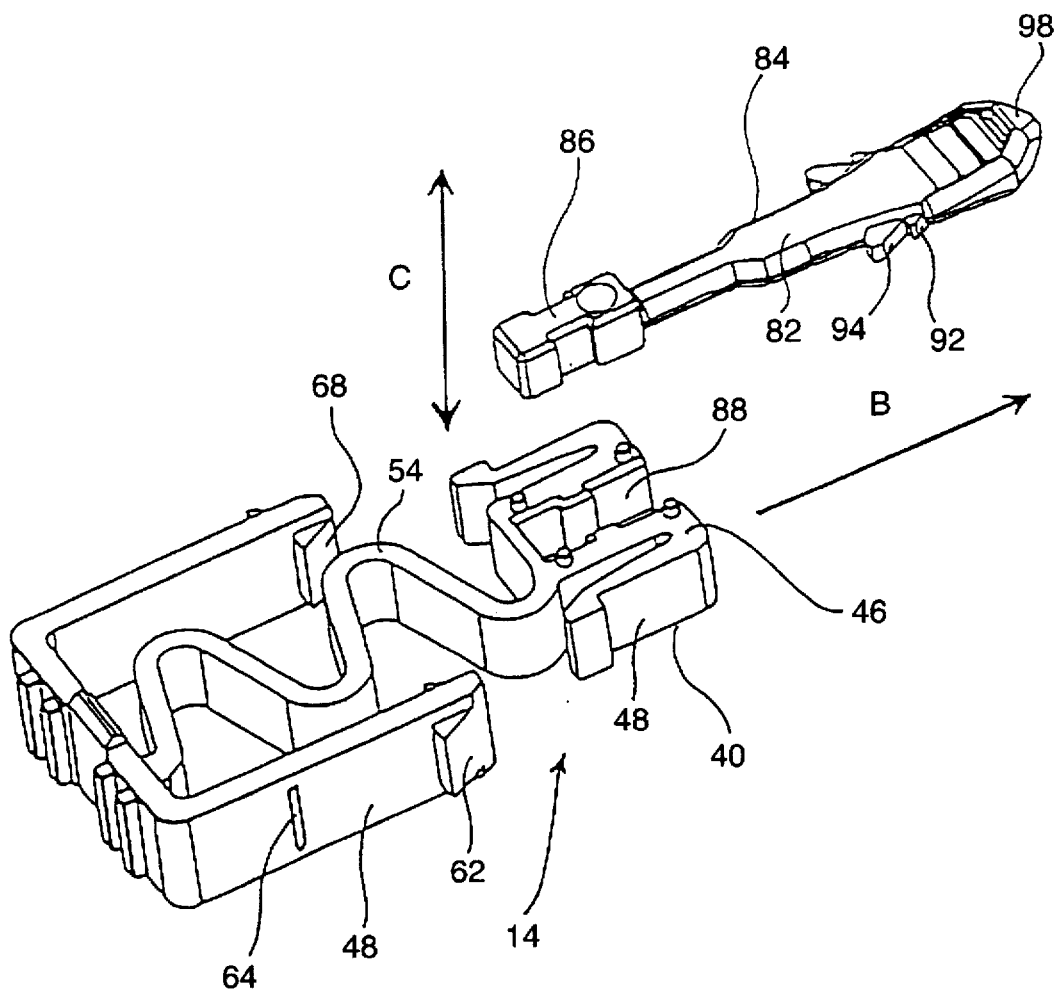
FIG. 10 schematically shows an exploded perspective view of a lancet structure of a lancet assembly of the second embodiment of the first aspect according to the present invention.

FIG. 10 schematically shows an exploded perspective view of lancet structure 14 of a lancet assembly of the second embodiment according to the first aspect of the present invention.

In the lancet structure 14, a lancet member 40 consists essentially of a lancet body 46 and a covered pricking member 84. The members 46 and 84 are separate from one another and are provided with engaging elements 88 and 86 which couple the members 46 and 84 together. As seen from FIG. 10, the lancet body 46 is integral with the spring member 54. Specifically, the covered pricking member 84 includes an engaging element 86 at an end thereof (opposite to an ejecting direction) which has an overall convex shape (male portion). The lancet body 46 includes an engaging element 88 which comprises an overall concave shape (female portion) at its end opposite the end connected to the spring member 54.

More specifically, as may be seen from FIG. 10, the lancet body 46 comprises the concave engaging element 88, and the covered pricking member 84 comprises the convex engaging element 86 at its end (a base portion) which mates with the concave engaging element 88 along a direction of the arrow C from an upper side downward (for example with press fitting). It is of course possible that the convex engaging element and the concave engaging element are exchanged with each other. As seen from the drawing, the convex and concave shapes of the engaging elements 86 and 88, respectively, are complementary to each other and couple the covered pricking member 84 and the lancet body 46 together such that they can withstand a tensile force along an ejection direction of the lancet body 46 (arrow B). For example, the lancet body 46 and the covered pricking member 84 may not be disconnected by merely applying a force with one's fingers. However, these members 46, 84 may be separated from one another upon application of a sufficient, relative vertical force applied in the direction of arrow C.

The engaging elements 86 and 88 may be in any complementary forms provided that the members including the elements withstand the force of the arrow B and they are combined substantially along the direction of arrow C to achieve the engaging relationship. Generally, the engaging elements may be formed by combining various sets of complementary concave and convex portions.

In order to form a covered pricking member 84, the resin cover may be formed on the pricking member 44 to form a covered pricking member 84 by, for example, an injection molding process. The cavities of metal molds may be arranged to provide an optimal configuration of the covered pricking member 84 when the lancet body 46 is combined or mated therewith.

For example, a portion of the covered pricking member 84, preferably an end or base portion 86 thereof, may be so arranged that its configuration is suitable for the connection to the engaging element 88 of the lancet body 46 with any suitable manner such as press fitting, snap fitting, and optional ultrasonic welding or caulking thereafter (in which case the lancet body 46 cannot be separated from the covered pricking member 84 once they are connected together).

It is also preferred that the configuration of the resin covered pricking member 84 is suitable for mechanical manipulation or processing. For example, a partially wide configuration (for example, at an end portion) is advantageous in that the covered pricking member 84 may be easily picked up using a mechanical chuck or an air chuck for the incorporation of the covered pricking member 84 into the lancet body 46.

This is in contrast to prior art devices which are produced by incorporating a metal (stainless steel in most cases) blade itself as a single member into a lancet body. In as much as a stainless steel blade is small and light (typically 2.5 mm width×12 mm length×0.16 mm thickness and 0.28 to 0.30 g per blade), it is more likely that a typical "picking up" means, such as the air chuck or mechanical chuck, would fail to pick up a single blade (as in the prior art) than the inventive covered pricking member 84 when incorporating the blade into the lancet body. In addition, it is more difficult to transport a blade for incorporation into the lancet body because the blade is light and magnetized, and, as a result, the blade will not fall in a stable manner when released.

In addition, the only possible manners (as explained with reference to FIGS. 6 and 7) by which the pricking member 44 could be directly incorporated and connected to the lancet body 46 have been to use an adhesive or to partially heat-deform an objective member (i.e. the lancet body 46). These manners are not suitable for mass production.

In contrast, according to the present invention, the pricking member 44 (visible in FIGS. 17–18) is covered with resin to produce a separate covered pricking member 84. A portion of the member 84 is so (widely) configured that it is suitable for picking up, whereby its configuration becomes suitable for the incorporation onto the lancet body as described above. Thus, the covered pricking member 84 (the structure including the blade) results in a more optimal size, a more optimal weight, cancellation of a magnetic force effect and a more suitable shape for picking up, transferring, releasing, incorporating the covered pricking member into and connecting it to the lancet body in comparison with the use of a single blade itself. As a result, it is possible to continuously incorporate the member 84 onto the lancet body 46 accurately and stably using an automatic machine.

Further, it is possible to use a manner to connect the resin covered pricking member 84 to the lancet body 46 that is suitable for continuous mass production, as, for example, by press fitting, snap fitting, ultrasonic welding or caulking. These manners are superior to the case in which the blade alone is incorporated with respect to connection accuracy and connection strength.

With respect to the lancet structure of the second embodiment according to the first aspect of the present invention, covering the pricking member with the resin, and forming it into the desired covered pricking member 84 shape can be continuously and automatically carried out in a clean room. The processing may be performed by endless insert hoop molding and metal molds fabricated for the formation of the desired shape lancet structure shape in the case in which the pricking member 44 is in the form of a blade, or by an automatically inserting (machine in the case in which the pricking member 44 is in the form of a needle). The possibility of the mass production and the reduced overall cost are very important factors for devices which are used for medical treatments in high volumes.

Figure 11:
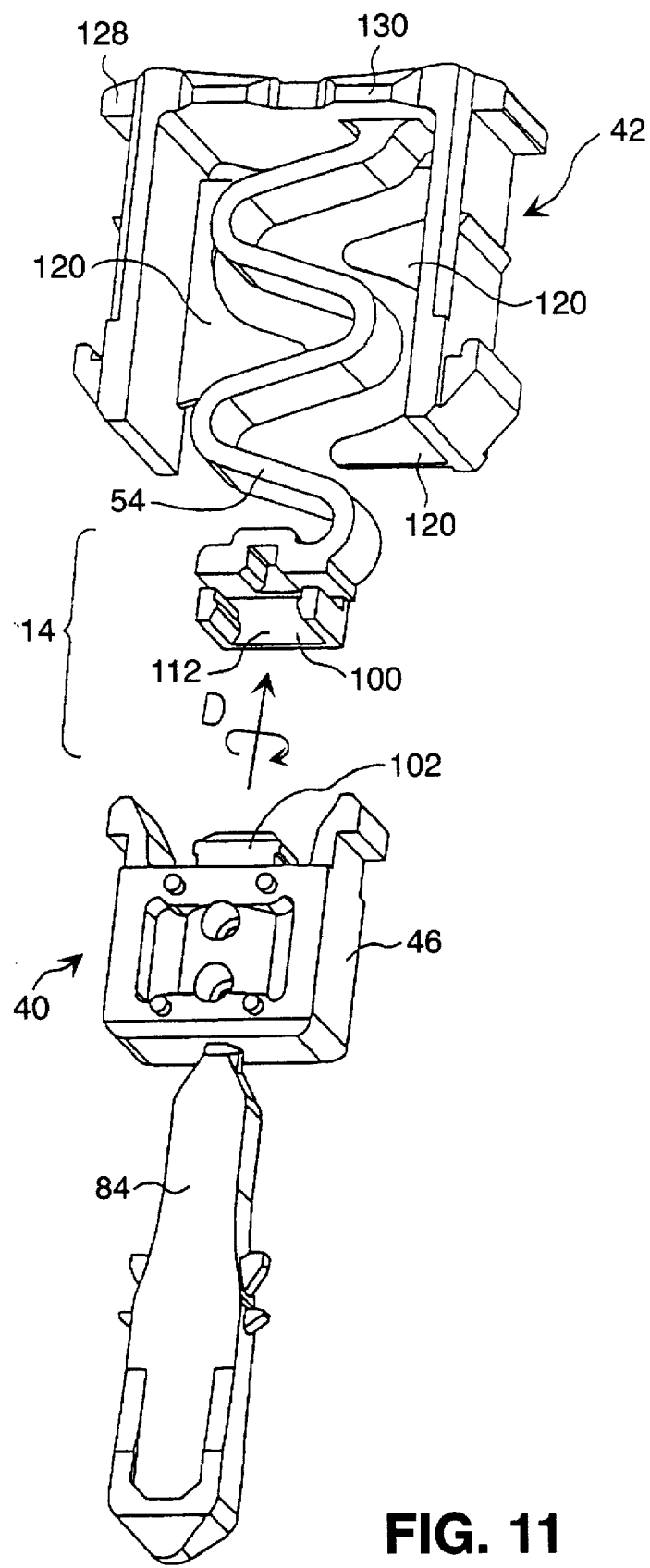
FIG. 11 schematically shows an exploded perspective view of a lancet structure of a lancet assembly of the third embodiment of the first aspect according to the present invention.
Figure 12:
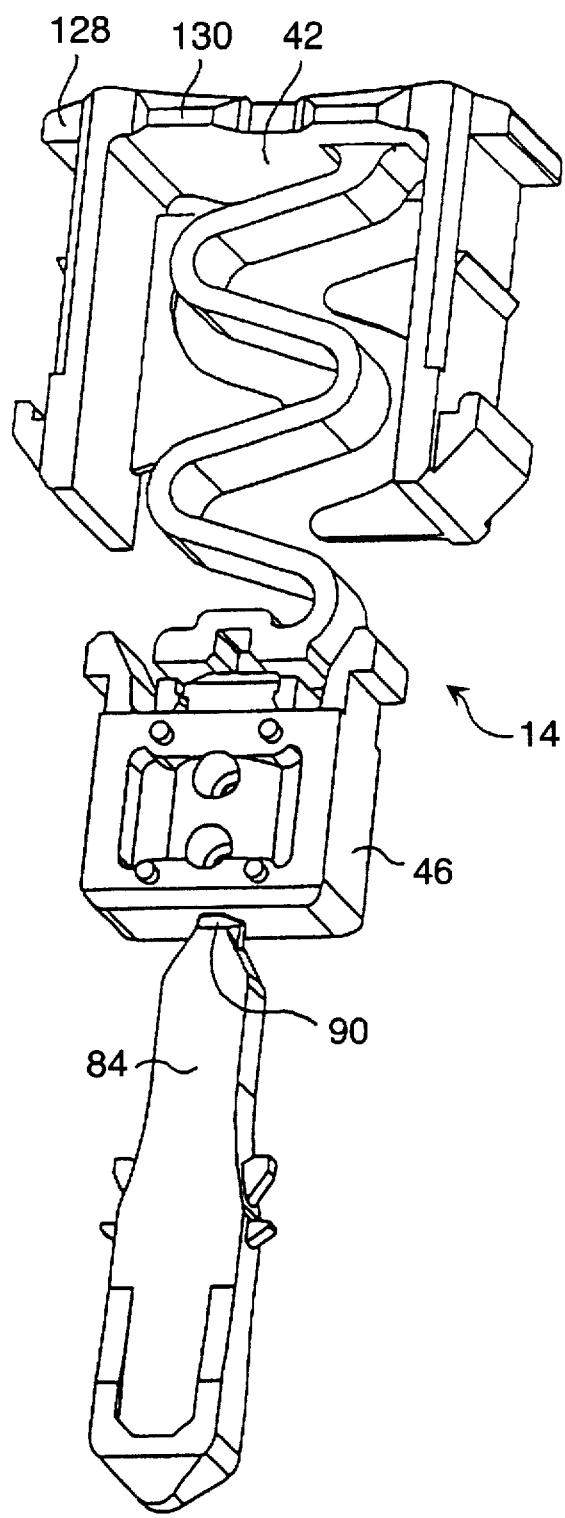
FIG. 12 schematically shows a perspective view of a position of FIG. 11 after assembling.

A lancet structure 14 of the third embodiment according to the first aspect of the present invention is shown in a perspective view in FIG. 11 before connecting the ejector 42 and the lancet member 40 and in FIG. 12 after connecting them. As seen from these drawings, the lancet structure 14 in the third embodiment comprises the ejector and the lancet member 40 which are separated from each other, and the lancet member 40 comprises the pricking member 44 which is covered with resin (namely, the covered pricking member 84) and the lancet body which is integral with the covered pricking member 84. Connection between the ejector 42 and the lancet body 46 is achieved by snap fitting of a snap fitting female member 100 in the form of an overall concave (which is located at the end of the spring member 54) and a snap fitting male member 102 in the form of an overall convex (which is located opposite the connection to the covered pricking member 84 of the lancet body 46) along a direction of the arrow D. Namely, the lancet body 46 and the ejector have portions which mate with each other (100 and 102).

Figure 13:
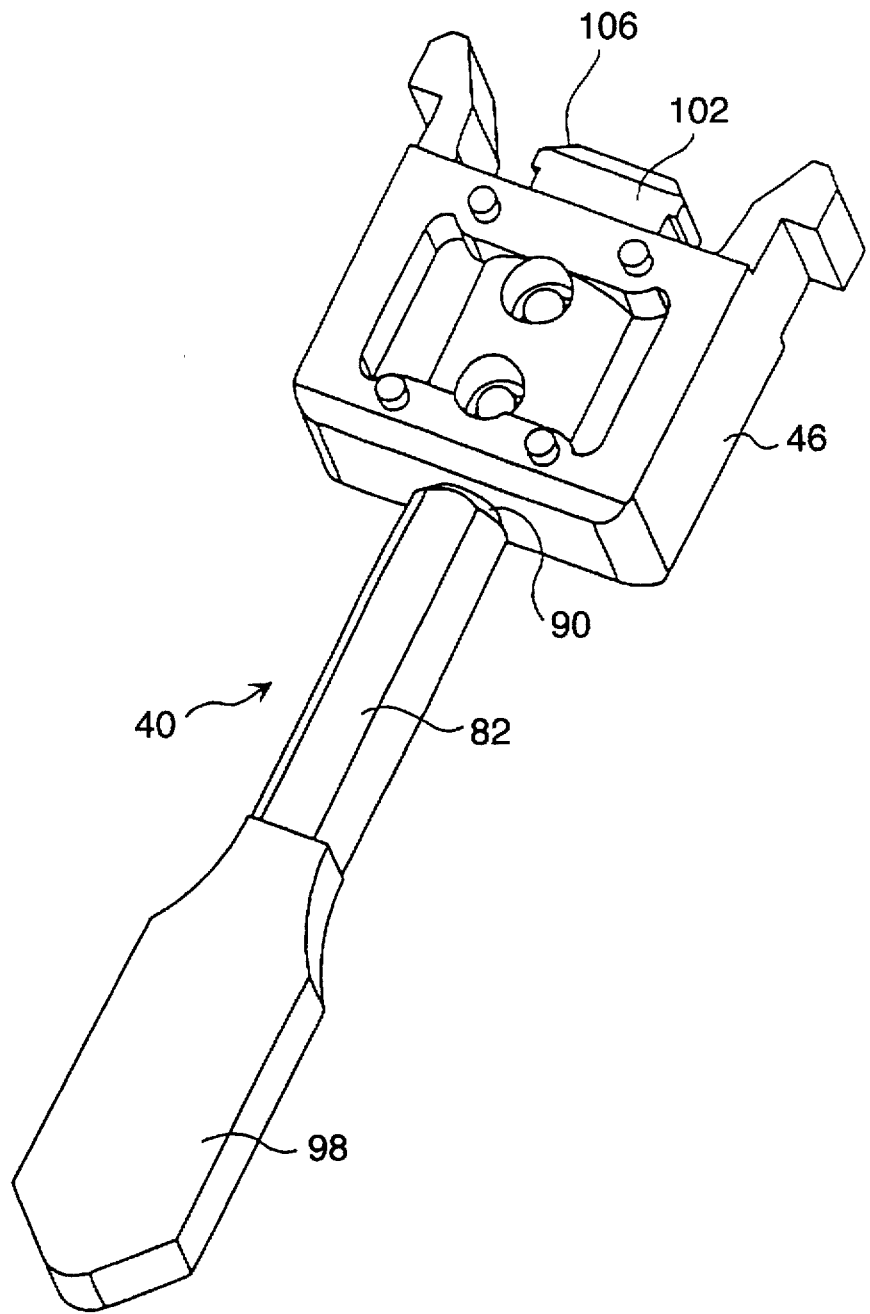
FIG. 13 schematically shows a perspective view of a lancet member which is used for the lancet structure of the lancet assembly of the third embodiment of the first aspect according to the present invention.
Figure 14:
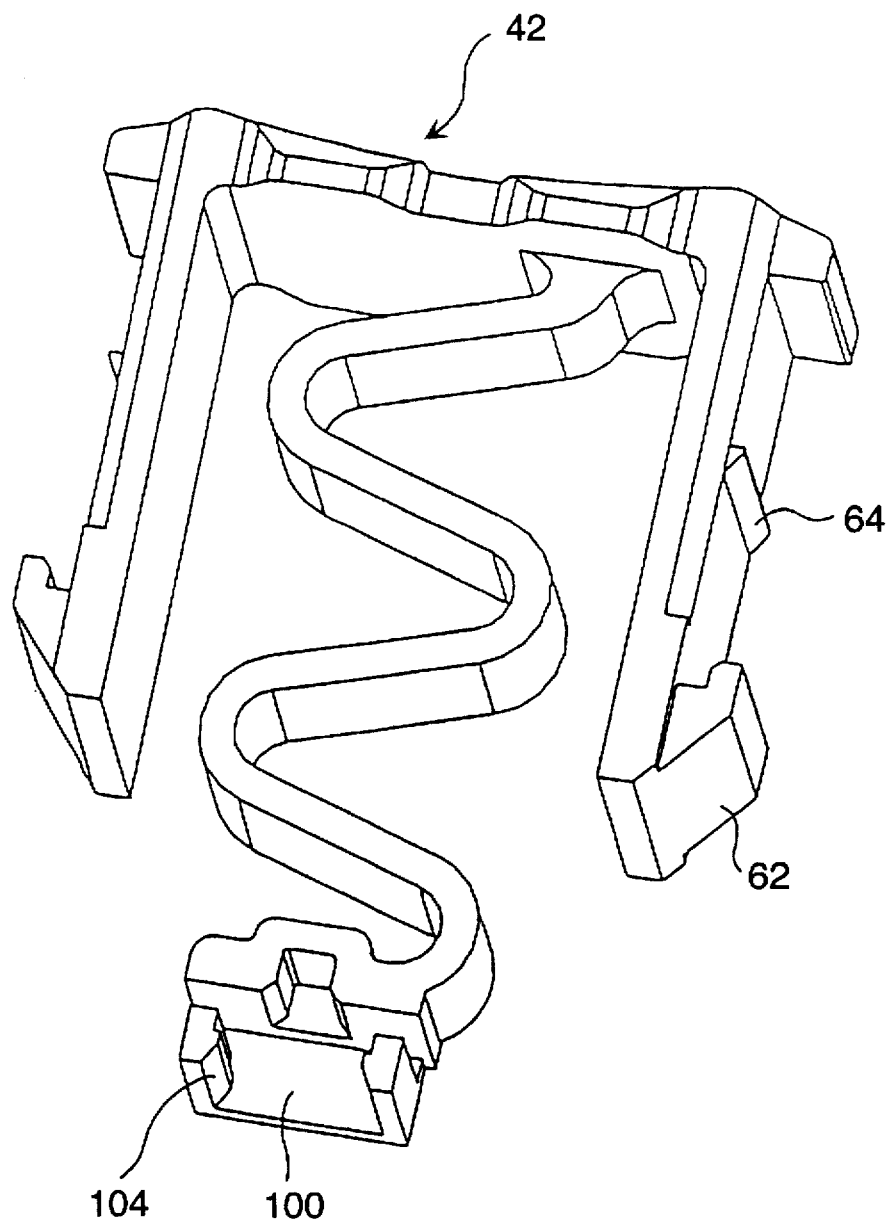
FIG. 14 schematically shows a perspective view of an ejector which is used for the lancet structure of the lancet assembly of the third embodiment of the first aspect according to the present invention.

The lancet member 40 and the ejector 42 are schematically shown in FIGS. 13 and 14, respectively. As seen from these drawings, edges 104 of the female member and edges 106 of the male member have outwardly tapered surfaces 104 and inwardly tapered surfaces 106, respectively, which help fitting of the concave member into the convex member upon snap fitting along a direction of the arrow D (in FIG. 11). Namely, the convex member 102 guides insertion of the concave member 100. The female member 100 and the male member 102 are made of a plastic material, and it becomes possible for the male member to pass through an opening of the female member 100 since the opening is transiently enlarged due to elasticity of the plastic material, and the opening returns to its original shape after passing. Mating with snap fitting may be possible even with an extremely small force when tapering angles and the material are properly selected. In the embodiment shown in FIG. 14, lips 68 are omitted, but they may be present as described above with reference to the prior art structure.

On the other hand, corner portions on surfaces opposite the tapered surfaces having the female member 100 and the male member 102 is of a substantially right angle. Thus, once the ejector 42 and the lancet member 40 are connected together with snap fitting, such they remain connected even if a force is applied in an attempt to separate them from each other (for example, along a direction opposite the arrow D in FIG. 11) provided that the force is not large enough to deform or break the plastic material. The corner portions are not necessarily of a right angle, and those members may be disconnected when a certain predetermined force is acted. However, the material and the shape should be selected so as to ensure that the lancet body 40 is not disconnected from the ejector 42 when the lancet body 40 retracts after it has been ejected.

Shapes of the female member 100 and the male member 102 are not particularly limited and they are sufficient if snap fitting is possible between them. For example, the lancet member 40 may include the female member and the ejector 42 may include the male member. In the third embodiment as above, the direction along which the ejector 42 and the lancet member 40 are assembled during the formation of the lancet structure may be the same direction (a direction of the arrow D in FIG. 11) which is achieved by rotating the assembling direction of the second embodiment (a direction of the arrow C in FIG. 10) around an ejecting direction.

The assembling direction of the lancet assembly of the third embodiment has the following advantage:

In order to produce the lancet assembly as a final product, the lancet structure 14 should be fitted into the holder 16. In the first and the second embodiments, the lancet structure 14 is formed beforehand outside the holder 16, and then thus formed lancet structure 14 is incorporated into the holder 16. In the third embodiment, two features can be utilized: one is that the assembling direction of the lancet structure 14 (a direction of the arrow D in FIG. 11) substantially corresponds to a insertion direction of the lancet structure into the holder (a direction of the arrow A in FIG. 2); and the other is that connection of the ejector 42 and the lancet member 40 is easily achieved as described above.

Figure 15:
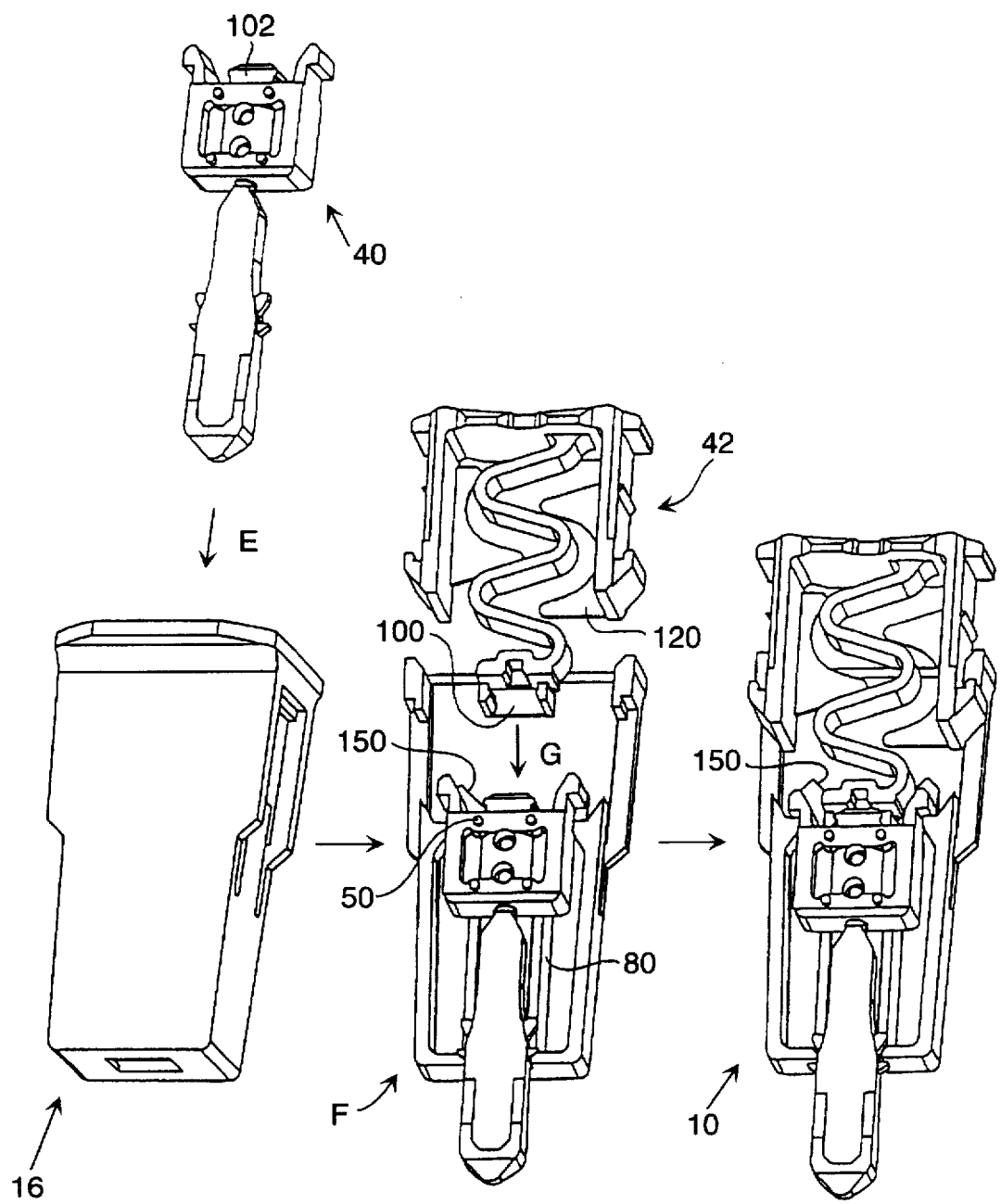
FIG. 15 schematically shows assembling of the lancet assembly of the third embodiment of the first aspect according to the present invention.

As shown in FIG. 15, the lancet member 40 alone is first inserted into the holder 16 (along a direction of the arrow E) to achieve a position indicated with the arrow F (in the bottom center). For easy understanding, an upper half portion of the holder 16 is cut away in FIG. 15. Then, depression of the ejector 42 into the holder 16 along a direction of the arrow G causes the lancet member 40 and the ejector to connect with a snap fitting as shown in the right side of FIG. 15. When the depression is manually carried out, one feels the snap fitting. When the depression is carried out with a machine, the distance which the machine depresses the ejector 42 into the holder 16 can be set beforehand to complete snap fitting. Such that the machine can depress the ejector 42 over the certain distance. The third embodiment does not require to performing of the lancet structure 14, but has an advantage that the lancet assembly according to the present invention is automatically formed by first inserting the lancet member into the holder, and then disposing and depressing the ejector into the holder.

The female member 100 has a bottom portion 112 (see FIG. 11). However, the female member 100 and the male member 102 are so arranged that the same lancet structure 14 is produced whether the ejector 42 is engaged with the lancet member 40 along a direction of the arrow D as shown in FIG. 11 or the ejector 42 is engaged with the lancet member 40 in a position in which the ejector is rotated by 180° around the arrow D from the position shown in FIG. 11 (namely, a position in which the bottom portion 112 becomes a top portion).

Figure 16:
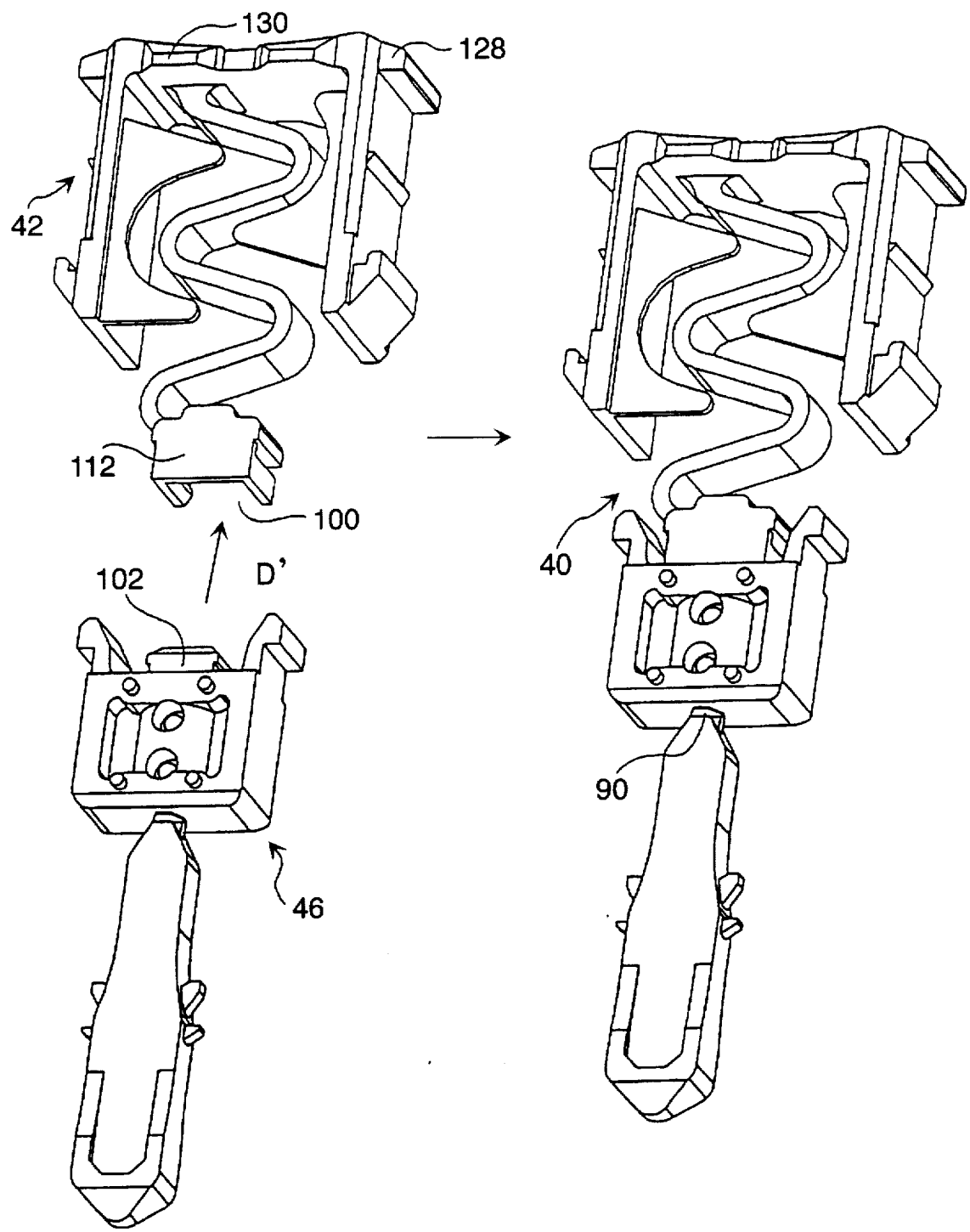
FIG. 16 schematically shows another assembling of a lancet structure of the third embodiment of the first aspect according to the present invention.

Such position of the lancet member 40 and the ejector 42 is shown in FIG. 16. Therefore, no attention has to be paid to a front or back surface of members (relative to paper surface of FIG. 16) with respect to an orientation at which the lancet member 40 is inserted into the holder 16 and an orientation at which the ejector 42 is inserted into the holder 16. This leads to the following advantage: When the lancet assembly 10 is assembled in the manner shown in FIG. 15, the lancet member 40 is inserted into the holder 16 (for example, dropped using gravity) such that the covered pricking member 84 is directed downward with merely an attention to the ejection direction, and no attention has to be paid with regard to the front side or the back side of the paper of FIG. 15. This is also applicable to the ejector 42 and the holder 16. This advantage leads to no detection of the orientation (namely, the front side and the back side) of the members 16, 40 and 42 when automatic assembly is carried out. As seen from FIG. 15, since the channels 80 have tapered portions 150 at their ends which open upwardly, merely dropping the lancet member 40 guides the pins 50 into the channels 80, resulting in proper positioning of the lancet member 40 in the holder 16.

It is, of course, possible to form the lancet structure 14 outside the holder 16 as in the case of the first or the second embodiment, followed by incorporation of the structure into the holder 16. In such case, the lancet structure may be formed along a direction of the lancet ejection (the arrow D) or the same direction as in that of the second embodiment (the arrow C).

When the covered pricking member 84 and the lancet body 46 are connected together as in the third embodiment, the resulting lancet member 40 has a larger size than, for example, the covered pricking member 84 of the second embodiment. This is advantageous in that the lancet member 40 is easily picked up and incorporated into the other member (such as the ejector 42) upon assembling, especially automatically assembling using a machine such as an auto feeder.

The lancet assembly of the third embodiment may be substantially the same as that of the first or the second embodiment except that the connection relationship between the lancet body 46, the covered pricking member 84 and the ejector 42. The shown embodiments are different in a length of the arm 48 and the presence or absence of the lips 68, which are not substantive.

The lancet structure 14 in the second and third embodiment comprised a separate, covered pricking member 84 or a separate elector. Thus, those separate members may be made of a different material from that of the other part. This has the following advantage when the functions of the ejector 42 and the covered pricking member 84 are considered:

The ejector 42 comprises the spring member 54, which should have a spring property. The spring property is referred to a property that when it is compressed, its length (along the compression direction) is shortened resulting in accumulation of energy (a repelling force), and when it is released from the compressed condition, its length transiently extends over its original length and then returns to its original length with recovering its original shape. A material having such a spring property includes plastic materials. Among them, engineering plastic materials are particularly preferable such as a polyamide, a polybutylene terephthalate and a polycarbonate. When those engineering plastic materials are used to unitarily form the lancet body 46 and the covered pricking member 84, the formation itself is carried out without difficult. However, even the notch is provided at a certain predetermined point for the removal of the cover resin by breaking the covered pricking member 84, a larger force is required than in the case in which general resins such as a polyethylene and a polypropylene are used, which may not be necessarily preferable. In addition, although the pricking member should be sterilized using for example γ-ray, the polycarbonate among the engineering plastics does not necessarily have sufficient resistance against γ-ray.

Considering the above breakage and sterilization issues, more preferable material includes the polyethylene material such as a high density polyethylene or a low density polyethylene. Thus, when the covered pricking member 84 is formed as the separate member using the polyethylene, those breakage and sterilization issues are solved. It is, of course, not necessarily desirable to form the ejector 42 using such a polyethylene material since its spring property is not necessarily sufficient compared with the formation with the engineering plastic materials as described above.

On the other hand, the lancet body 46 may be non-problematically formed of the material which is preferable for the ejector 42 or the material which is preferable for the covered pricking member 84. Then, the second embodiment in which the lancet structure 14 is composed of the unitary structure of the lancet body 46 and the ejector 42 and the separate covered pricking member 84, or third embodiment in which the lancet structure 14 is composed of the unitary structure of the lancet body 46 and the covered pricking member 84 and the separate ejector 42 is relatively more advantageous than the first embodiment in which all members are made of the same plastic material.

Further, when the second embodiment is compared with the third embodiment, the covered pricking member 84 is a separate member and relatively small in the second embodiment while, in the third embodiment, the separate and unitary lancet member 40 of the covered pricking member 84 and the lancet body 46, which is larger than the covered pricking member 84 alone. This makes handling (for example, picking up) of the member 40 easier, so that the third embodiment is preferable since the production and assembling of the member is facilitated.

The second embodiment is much easier than the prior art in which the exposed blade 44 is incorporated into the lancet body 46 as the blade is. However, the third embodiment in which the covered pricking member 84 and the lancet body are formed as the integrated member is easier in its handling, and the member is, therefore, advantageous in the connection with the ejector. In addition, it is also advantageous that the connection with the ejector 42 is not necessarily carried out in the holder beforehand.

In the fourth embodiment of the first aspect according to the present invention, an ejector 42, a lancet body 46 and a covered pricking member 84 are separate from one another. Those members have the engaging members (86, 88, 100 and 102) which have been described with reference to the second and the third embodiments (namely, the ejector 42 includes the members 100, the lancet body 46 includes the members 102 and 88, and the covered pricking member 84 includes the member 86). Those skilled in the art will easily understand the forth embodiment based on the explanations with respect to the embodiments as described above. When the fourth embodiment is compared with the second and the third embodiments, the former is not so advantageous as the latter two. However, compared with the prior art as in the case of the first embodiment, the fourth embodiment is more advantageous in that the exposed pricking member 44 is not handled alone, but as the covered pricking member 84.

In any embodiment of the lancet assembly according to the present invention, it is preferable that a notch (a cut-into portion) is provided in the resin cover 82 at a predetermined breaking position in order that only the cover 82 (substantially in the form of the sheath), which covers and protects the pricking member 44 of the lancet structure 14, can be broken and removed just before the use of the assembly.

The term "notch" as used herein is intended to mean a weakened portion (for example, a cut-into portion or a cut-away portion) of the resin cover which permits the resin cover to be broken at a predetermined position upon the application of a force along an ejection direction of the lancet body 46 having the pricking member 44 (for example, the arrow B in FIG. 10). Specifically a notch may be formed by partially thinning a portion of the resin cover 82 (namely, by providing a neck portion to the cover resin). More specifically, a U-shaped or V-shaped cross sectional portion is formed at an intended break position of the resin cover 82 (so that such a portion has a reduced thickness). In the preferred embodiments, the metal molds are so arranged that the notch is simultaneously formed when the cover resin 82 is molded, or a sharp blade is used to cut a notch into the resin cover 82 after molding the resin covered pricking member 84. It is of course possible to form the notch upon molding and to then further cut into the notch.

Figure 2:
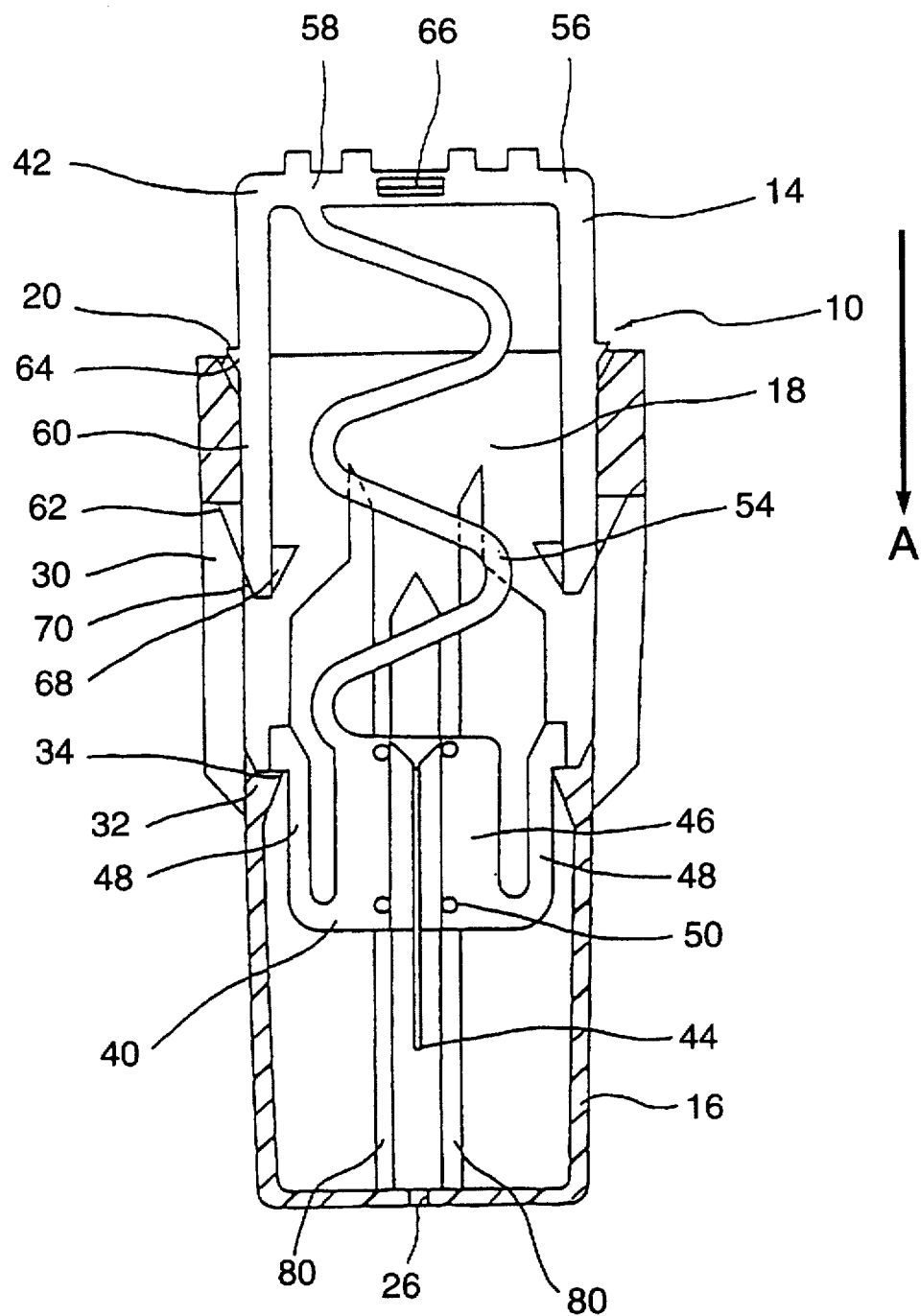
FIG. 2 schematically shows a front view of a position in FIG. 1 in which only the holder 16 is shown in a cross-sectional view in order that a position of the lancet structure 14 can be clearly understood.
Figure 3:
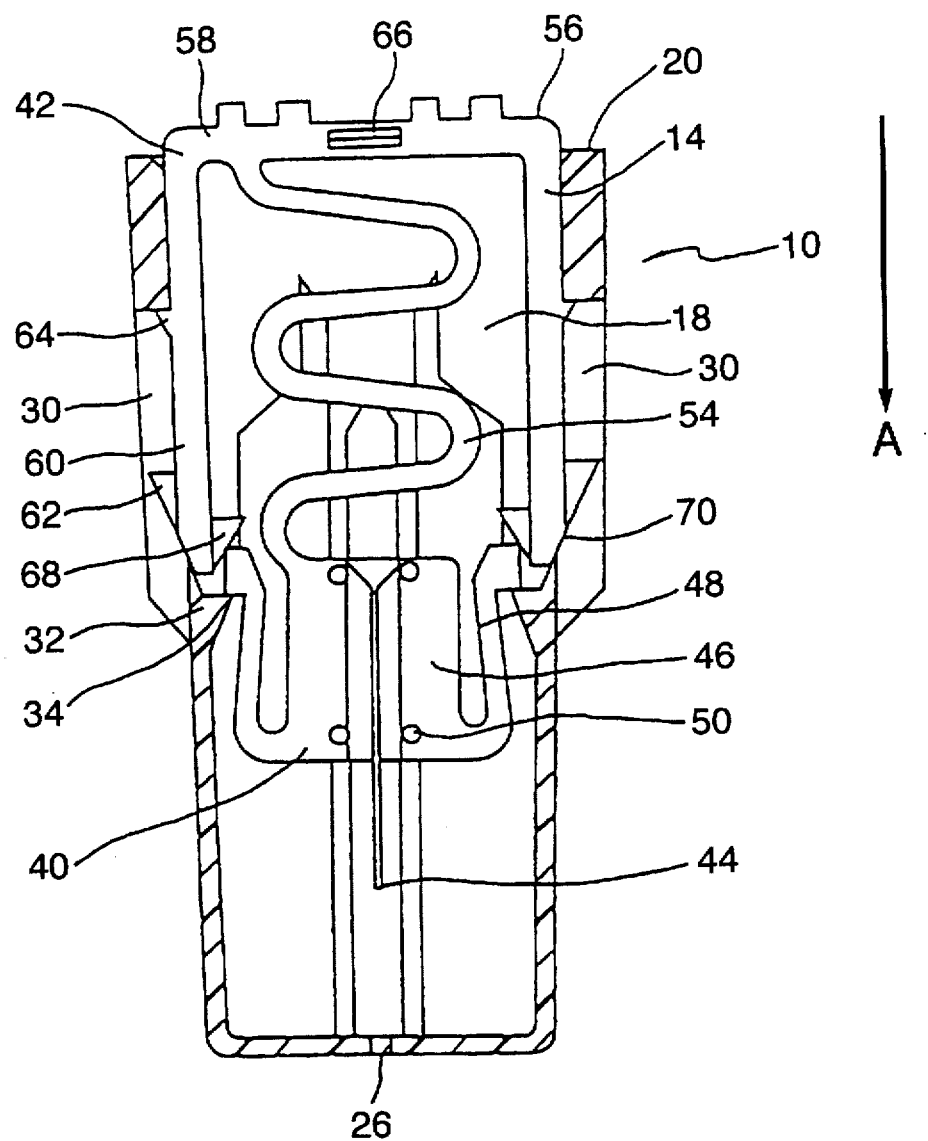
FIG. 3 is a schematic front view similar to the view shown in FIG. 2 wherein the lancet structure 14 is disposed inside of the holder 16.
Figure 4:
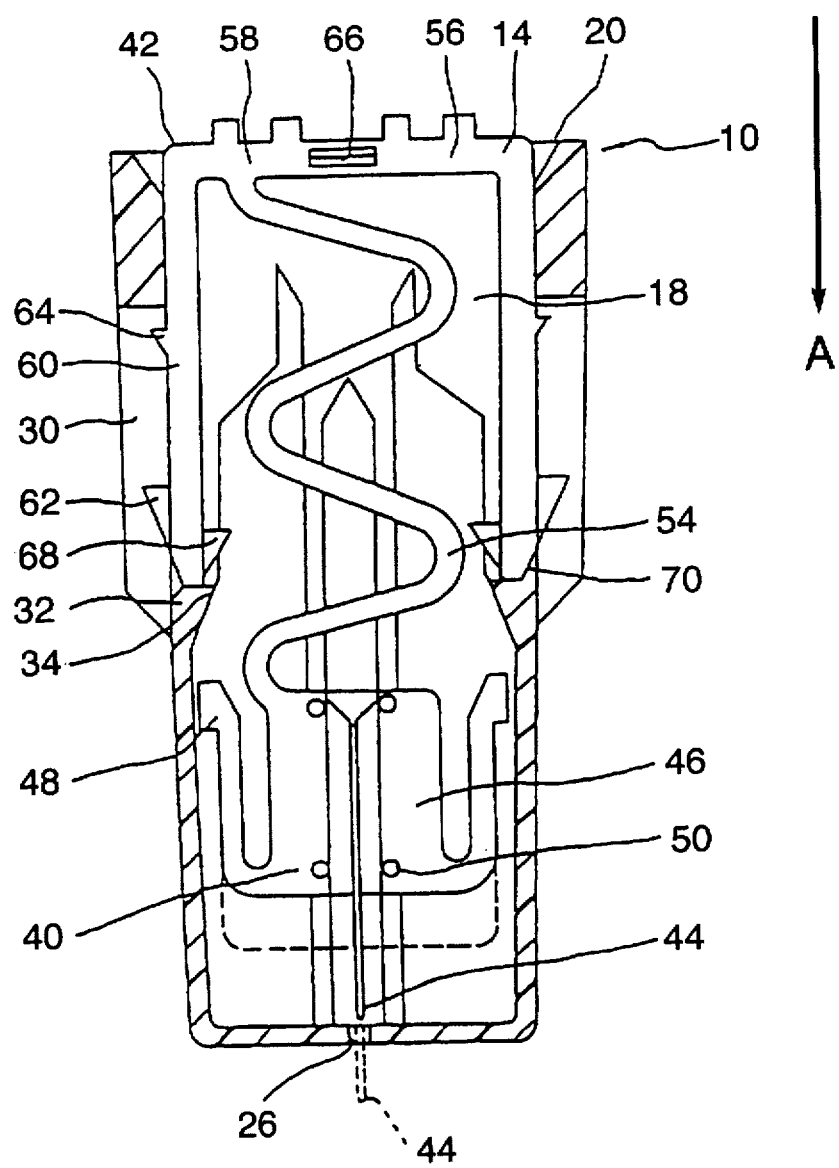
FIG. 4 is a schematic front view similar to the view shown in FIG. 2 showing a position of the lancet structure 14 being ejected for use.
Figure 5:
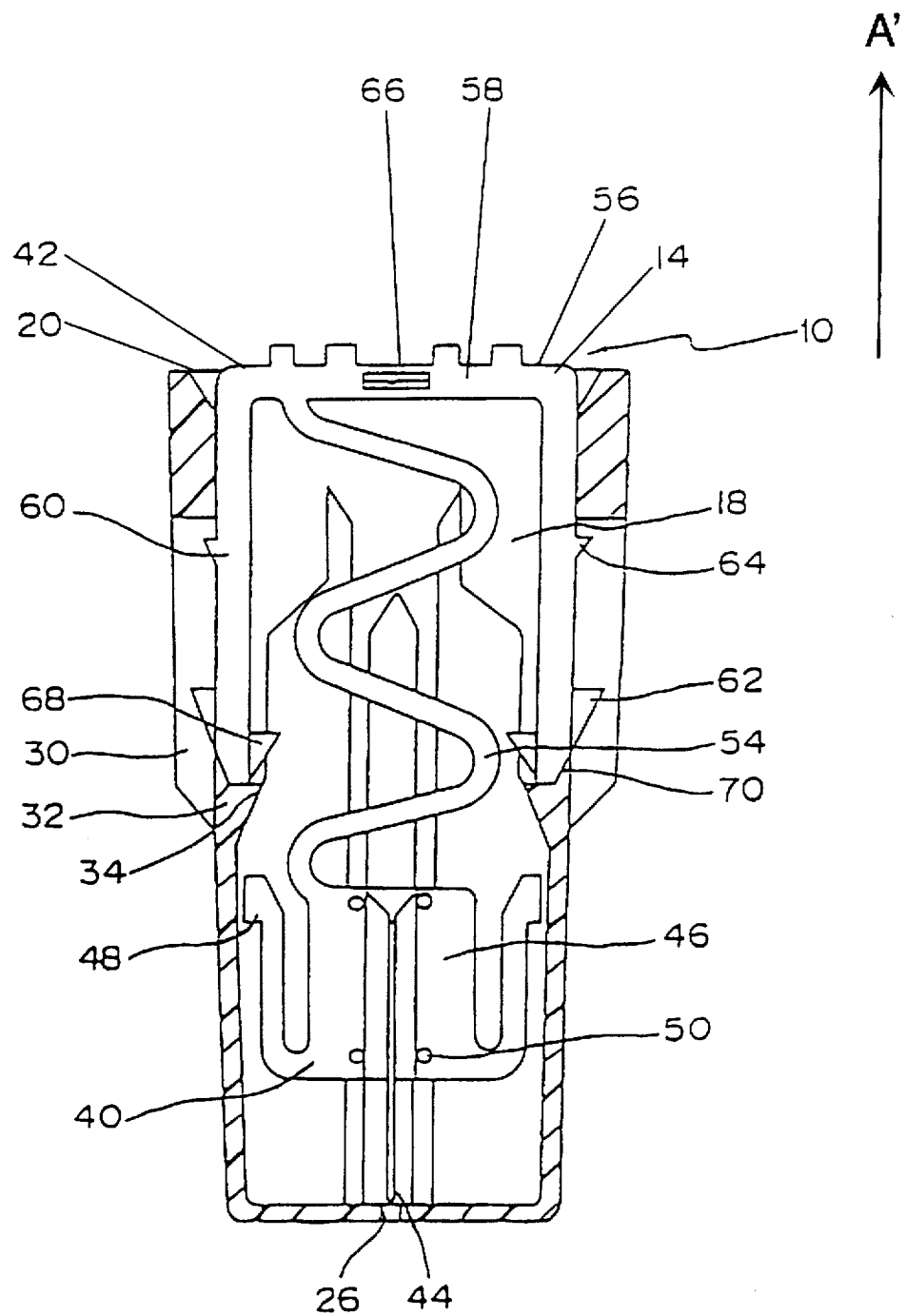
FIG. 5 is a schematic front view similar to the view shown in FIG. 2 showing a position of the lancet structure 14 after use.
Figure 17:
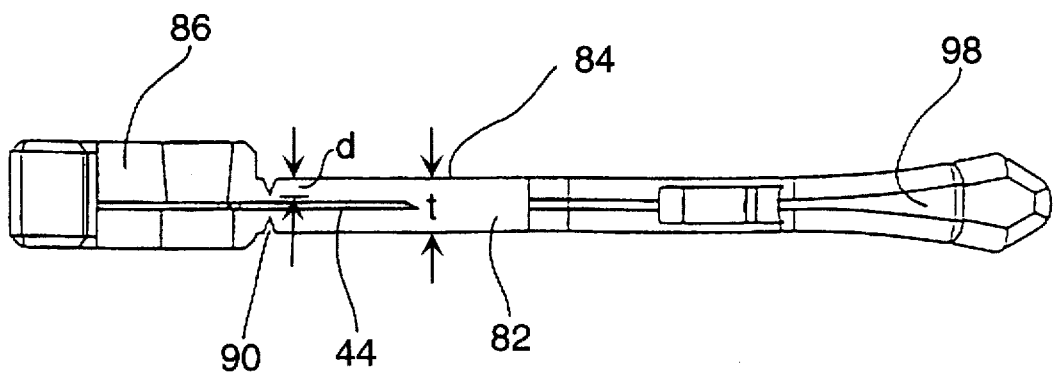
FIG. 17 schematically shows a partially cut-away side view of a preferable embodiment of the lancet assembly in which a covered pricking member has a notch.
Figure 18:
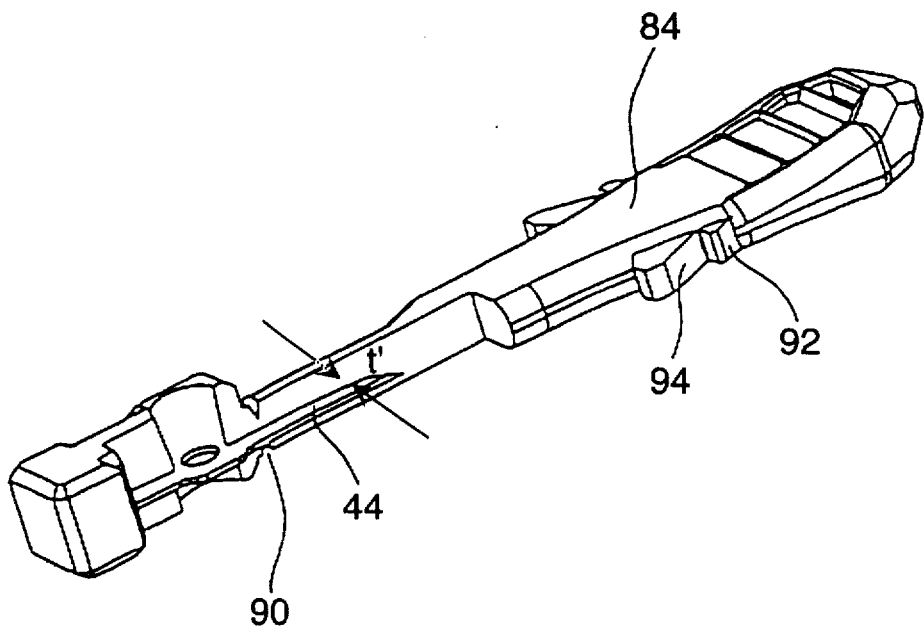
FIG. 18 shows a partially cut-away perspective view of the pricking member of FIG. 17.

An embodiment in which the resin cover comprises notches is shown in FIGS. 17 and 18, which schematically show a side view and a perspective view, respectively, of a resin covered pricking member 84 of the second embodiment according to the present invention (in FIGS. 17 and 18, the member is shown partially cut away to show the position of the pricking member 44). As seen from FIGS. 17 and 18, the pricking member 44 is rotated by 90° around an axis along the ejection direction as compared to the position of the pricking member 44 shown in the prior art lancet assembly of FIG. 2. The orientation of the pricking member 44 shown in FIGS. 17 and 18 is preferable in order to provide a compact construction of lancet assembly, but other orientations of the pricking member may be possible. For example, the orientation as shown in FIG. 2 may be employed.

As clearly seen from FIGS. 17 and 18, the notches 90 are formed at the predetermined break position of the resin cover 82. The predetermined break position may be any proper position of the resin cover, provided that breaking the resin cover 82 exposes at least the tip portion of the pricking member 44. At least one notch is formed into at least one of the opposing main (front and back) surfaces of the cover, which notch is usually perpendicular to the ejection direction of the lancet structure. In a preferred embodiment, the notches 90 are formed on the both surfaces of the resin symmetrically to the pricking member 44 as shown in the drawings. Usually, it is suitable that the notches 90 are formed near the lancet body 46. The provision of the notches is applicable to any embodiment of the present invention described above.

The notch 90 is preferably formed using a tool having a sharp edge (for example, a razor blade) after the resin cover 82 has been molded around the pricking member 44. A depth of the notch 90 ("d" in FIG. 17) is controlled so that an end (or a bottom) of the notch 90 does not reach the pricking member 44 which has to be surely kept in a sterile condition just prior to use. Thus, the sterile condition of the shielded blade 44 is assured prior to use of the assembly.

A practical thickness ("t" in FIG. 17) of the resin cover 82 which covers the pricking member 44 is in the range of about 1.4 to 2.0 mm, and it is thus sufficient that the depth of the notch ("d" in FIG. 17) is in the range of about 0.3 to 0.4 mm. It has been confirmed experimentally that the provision of the notch, in principle, makes the break strength of the cover sharply decrease regardless of the depth of the notch when any resin is used for the cover 82.

Although the notch may be formed by the metal molds upon the molding as described above, the effect of the provision of the notch is more pronounced when the notch is formed with the tool after molding.

The effect of the notch of the present invention described above is preferably achieved when the pricking member 44 is in the form of the blade, namely when the pricking member is thin and its cross section is substantially rectangular.

In a prior art lancet assembly using the pricking member in the form of the needle, a resin made member 82 cap protecting the needle can be removed from a body by twisting it just before use so as to break the resin. Such a prior art needle type lancet is so configured that a "neck portion" is provided at an intended break position to easily break the resin by twisting the cap.

Such a "neck portion" can be regarded as a kind of "notch". The "neck portion" corresponds to an embodiment in which a plurality of the "notches" are provided around the cover resin, and preferably to increasing the number of the notches, which leads to provision of a substantially peripheral recess (channel) around the resin cover. The notches are provided on at least one side of the pricking member and preferably on opposing sides thereof whether the pricking member 44 is in the form of a needle or a blade. There is, thus, no problem in the provision of more notches, and particularly in the needle type pricking member, three or more notches may be provided around the resin cover. In the embodiment shown in FIG. 13, a lancet member 40 of which pricking member is in the form of a needle and a channel 90 is provided around a whole periphery of the resin cover 82 just near the connection at which the resin cover 82 is connected to the lancet body 46. In such case, the resin can be broken by picking and twisting a tip portion 98 of the resin cover 98. Therefore, in order that such twisting is made possible, stops which will be explained below are omitted.

Since the cross section of the blade in a blade type lancet assembly is not circular but rectangular (a typical cross section is 2.5 mm width×0.16 mm thickness), it is impossible to twist the cover resin around the blade. Accordingly, it is impossible to twist the assembly in order to break the resin as in the case of the needle type lancet assembly. Therefore, in a blade type lancet assembly, it is essential that the user be able to easily break the resin cover at a predetermined break position and pull off the sheath-like resin cover in a manner other than twisting the resin cover, and the provision of the notch is very effective.

In the case of the needle type lancet assembly, since it is said that a force to break and pull apart the resin cover 82 (a tensile force along a direction of the arrow B in FIG. 10) is in the range of about 0.3 to 0.5 kg after twisting, the predetermined standard force required for breaking in a blade type lancet assembly would optimally be at similar force levels.

In order to achieve such a predetermined force for breaking the resin cover, the inventor produced the blades from a stainless steel plate and metal molds for injection molding of the covered pricking members and used them to produce some kinds of the blade structures which were covered with a polyethylene resin while inserting the blades (size: 0.16 mm thickness×2.5 mm width×12 mm length) insides the molds (i.e. covered pricking member 84). The blade structures were then tested. The inventor has found that resin covers in which the notch 90 was formed at the predetermined break point (see, for example, FIG. 17) in a region adjacent to the engaging element 86 using a proper tool (a razor blade of which edge was blunted was used in the tests) required a less force for breaking.

For the tests, four types of the resin covered pricking members 84 were produced. Two types had two notches, one each provided on an upper side and a bottom side of the covered pricking member, which were molded at predetermined break positions using the metal molds; the thicknesses of the neck portion, including the blade thickness (i.e. "t-2d"), were 1.2 mm and 1.6 mm, respectively. Two types had two notches, one each provided on an upper side and a bottom side of the pricking member, which were cut into the molded resin at the predetermined break positions using a razor blade (i.e. notches were not molded into the resin cover); the depths "d" of the notches were 0.3 mm and 0.5 mm, respectively. The cover resin used was a linear low density polyethylene. The thickness "t" of a portion of a resin covered pricking member without the notch (including the thickness of the blade) was 2.2 mm as a whole. A thickness "t" of the cover resin which is perpendicular to the thickness "t" and also perpendicular to the ejection direction (see FIG. 18) was about 0.4 mm at the notches 90. A tensile tester was used to measure the force required to break the resin cover.

(Test Results)

TEST (1): Each resin cover having molded notches was broken at the notches. The average force required to break 10 pieces was about 1.8 kg for 1.2 mm neck thickness, and about 2.0 kg for 1.6 mm neck thickness.

TEST (2): Each resin cover having notches cut in the molded part using a razor blade was broken at the notches. The average force required to break 10 pieces was in the range of about 0.3 to 0.4 kg and there was no clear dependency on the depth of the notch.

TEST (3): When a shallow (or short) rift (0.1 to 0.2 mm in length) was further formed at the notch which had been formed on the molding using a razor blade, a force required for the break was reduced to 0.25 to 0.3 kg.

TEST (4): The tensile tests were carried out without the formation of the notches. In the tests, the resin was stretched or broken at a position which was not indented.

From the above results, it has been found that the formation of the notch(es) at the predetermined break position is very effective, that the notch formed with the razor blade is more advantageous than that formed during the molding (namely, a sharper notch is particularly effective), and especially that the additional notch formation after the molding with notch formation is more effective.

Thus, it has been confirmed that, by using a proper tool to form a notch at a predetermined break position of the blade structure in a premolded resin cover, where the notch has a depth which does not adversely affect the sterile condition of the blade member, the blade can be tightly sealed and the sterile condition of the blade can be kept just before its use, and the blade resin cover can be pulled away with a relatively small force.

The material for the resin cover is not limited to a polyethylene (PE) resin. An ABS resin, a polyamide (PA) resin or copolymers of these polymers may be used. However, the polyethylene resin is particularly preferred.

The depth of the notch may be selected depending on the material used, especially its strength.

In any embodiment of the lancet assembly according to the present invention, the resin cover 82 shielding the pricking member 44 preferably comprises two pairs of protrusions as stops. These stops are particularly useful when notch(es) is provided on the resin cover 82 so as to easily break the resin.

Figure 19:
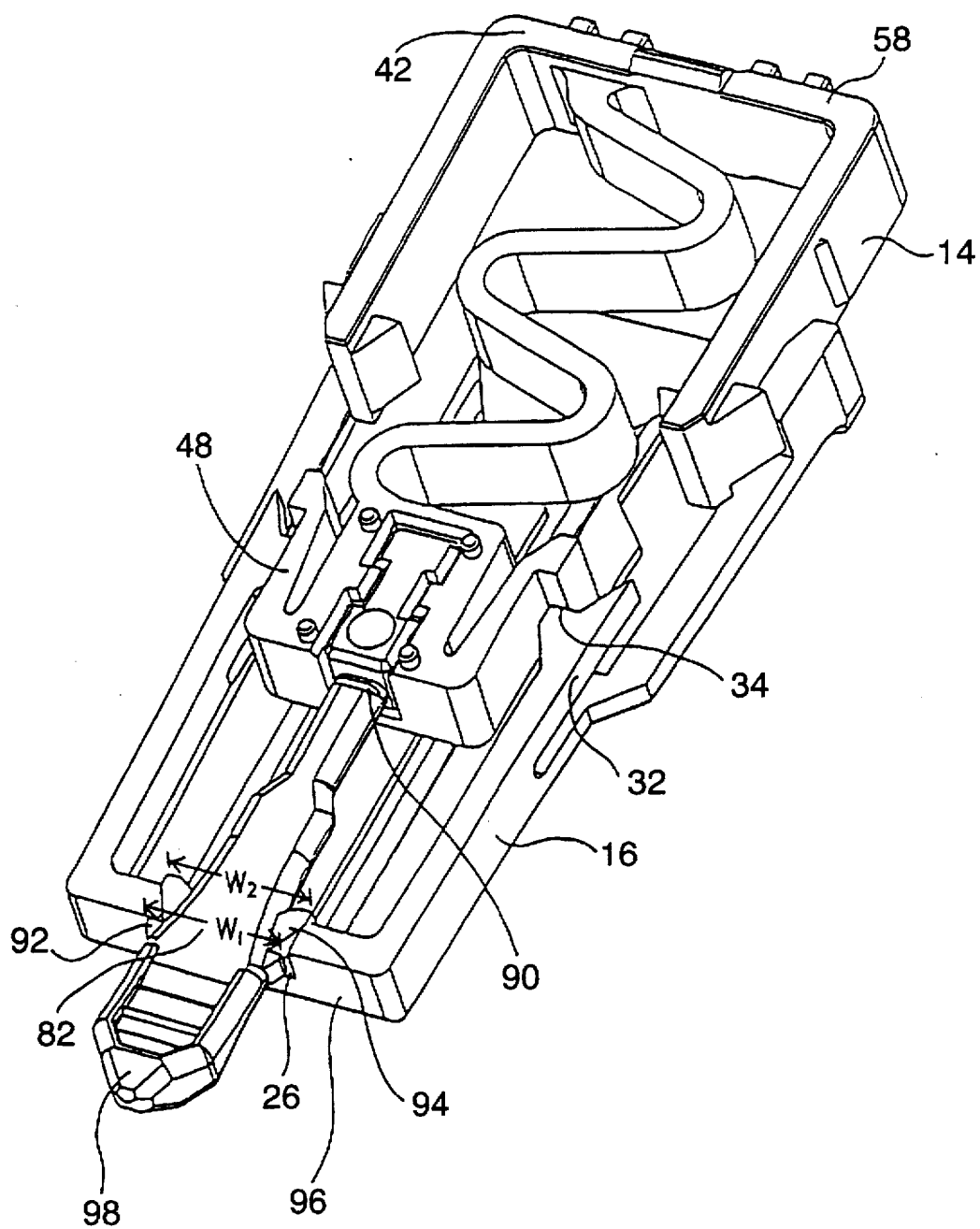
FIG. 19 schematically shows a perspective view of a preferred embodiment of a lancet assembly according to the present invention in which a covered pricking member includes two pairs of stops and an upper half portion of a holder is cut away so as to easily understand a position inside the holder.
Figure 20:
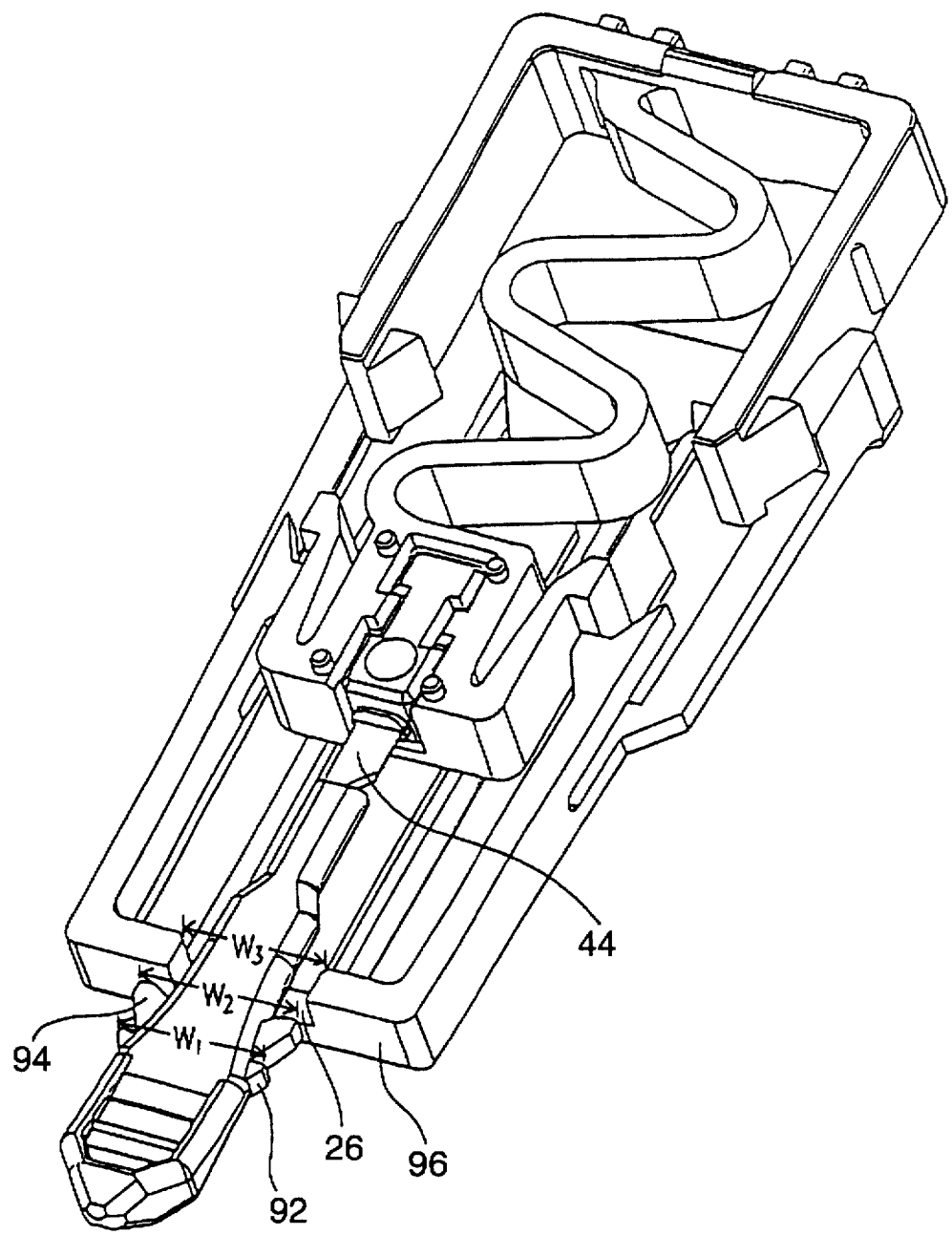
FIG. 20 shows a schematic perspective view similar to that shown in FIG. 19, wherein a covering resin is pulled off.

The resin cover 82 is likely to be broken and pulled away from the resin covered pricking member 84 along the notch due to the notch on the resin cover. In order that the sheath-like resin cover 82 is not easily removed from the lancet body 46 until it is pulled away for the use of the lancet assembly, the pairs of the stops (the first pair of the stops 92 and the second pair of stops 94) are provided on proper positions outside the resin covered pricking member 84 as shown in FIGS. 19 and 20. These two pairs of the stops also function to hold the sheath member 82 in place and keep such a position during final incorporation of the assembly. The embodiments shown in FIGS. 19 and 20 use the lancet structure of the second embodiment of the first aspect according to the present invention.

Further, these two pairs of the stops also function as an indicator which shows whether or not the sheath-like resin cover 82 is in place (namely, whether the resin cover 82 is properly connected to the lancet body 46) and thus whether or not the pricking member 44 remains sterile.

These protrusions are preferably in a double pair formation (i.e. the first row stops and the second row stops) as shown in the drawings which are generally protrusions from the resin cover member along a direction perpendicular to the ejection direction of the lancet body 46, and by positioning the end surface 96 of the holder 16 between the first and the second rows of the protrusions, the stops 92, 94 prevent the sheath-like resin cover from unduly being depressed into or pulled out of the holder 16. (As a result, the sheath-like resin cover 82 is prevented from being unduly broken at the notch portion.) The width of the stops (i.e. the distance between the outermost ends of the respective pairs of protrusions) in each of the first row and the second rows is larger than the width of the aperture 26 provided through the end surface 96 of the holder 16. For example, when the width of the aperture ($W_3$) is 4.8 mm, the width of the first stops ($W_1$) is in the range of about 4.9 to 5.0 mm, and the width of the second stops ($W_2$) is in the range of about 5.4 mm (see FIG. 20). Since the resin is resilient, the first stops 92 can pass through the aperture 26 when the lancet structure 14 is incorporated into the holder 16. The first stops 92 protrude through the aperture 26 with a force required for the arms 48 of the lancet body 40 to abut against the engaging protrusions 34 by depressing the lancet structure 14 into the holder 16 in the first, second or forth embodiment, or protrude through the aperture 26 by dropping down the lancet member 40 into the holder 16 or depressing the ejector 42 there after to achieve press fitting. The second stops 94 can also pass through the aperture 26, as shown in FIG. 20, when the resin cover 82 is removed just before the use of the lancet assembly. The protrusions are so shaped that their widths decrease along the ejection direction of the pricking member 44 so that the pricking member 44 cannot be reversibly depressed into the holder 16 once the protrusions has been outside the holder 16.

The provision of the protrusions results in the following three effects:

First, since the provision of the stops substantially fix the lancet structure 14, in particular the covered pricking member 84, in a position as shown in FIG. 19, the protrusions prevent accidental breakage of the sheath-like resin cover 82 at a position (or portion) of the notch 90 such as may result from various stresses (such as a force to pull out the covered resin of the holder, a force to twist the covered resin or a combined force thereof) continuously applied to the covered pricking member 84 during transportation of the lancet assembly 10. In this way, the sterile condition of the pricking member is stably and readily maintained.

As seen from the Examples set forth below, one hundred sets of lancet assemblies were produced according to the present invention, and 25 pieces per batch were placed in a paper box, which was then placed in a pan of an ultrasonic bowl feeder. The bowl feeder was continuously operated for one week and none of the resin covers 82 were broken or removed from the lancet structure, and all the pieces were normal.

Secondly, the stops visually indicate whether or not the sterile and normal condition of the pricking member 44 has been maintained prior to use.

When only the first stops 92 are exposed outside from the holder end surface 96 and the second stops 94 are inside the holder 16 so that they cannot be seen from the outside (as shown in FIG. 19), the resin cover is in place (namely, the assembly is intact) so that the resin cover has not been broken at the notch portion 90, whereby the pricking member 44 is kept sterile normally and safely (thus, since the lancet assembly is intact and safely in the sterile condition, it can be used for the usual application).

When the first stops 92 are not exposed outside the holder 16, such a position of the stops means an improper incorporation of the lancet assembly and such an assembly should not be used.

Further, when the first stops 92 and the second stops 94 are both exposed outside of the holder 16, such a position of the stops indicates that the resin cover 82 may be broken at the notch portion 90, which indicates that such a lancet assembly should not be used. This is clear from FIG. 20.

Therefore, the user should only use the lancet assembly in which the first stops 92 alone are exposed from the aperture 26 of the holder 16. Also during inspection of production of the lancet assemblies in the factory, a defective assembly can be rejected by means of the first stops as the indicator.

Since the structure containing the pricking member 44 is contained within the holder 16 in the present lancet assembly, visual observation is impossible to check the presence of the break at the notch portion. As a result, the presence of the indicator as described above is very important in that it visually indicates whether or not the blade is safely and normally protected.

With respect to the blade type assembly, when the force required to cause the second stops to pass through the holder aperture is larger than the force required to break the resin cover at the notch portion, desirable results are obtained. To produce such an assembly, the depth of the notch (a force required for the break) is selected first, then the size (in particular, its width) of the holder aperture, and then the size (in particular, its width) of the second stops relative to the aperture are made larger stepwise to determine an optimal size (i.e. an optimal resistive force on passing through the aperture) of the second stops.

Thirdly, the second stops prevent the sheath-like resin cover from being twisted in error.

As a general example for the stops and the aperture, when, for example, the height of the holder inside (namely, the length of the inside of the holder perpendicular to the ejection direction of the lancet structure and also perpendicular to the width direction of the stops) is 4.3 mm and the stops width is 5.4 mm, the covered pricking member 84 cannot be twisted (or turned) in the holder 16. This means that even though the user in error tries to twist the covered pricking member 84 so as to remove it, the member 84 is never twisted in the holder 16. This prevents serious defects such as bending and damaging of the pricking member 44 and also the break of the cover resin 82 due to unduly forced twisting of the member 84.

Figure 1:
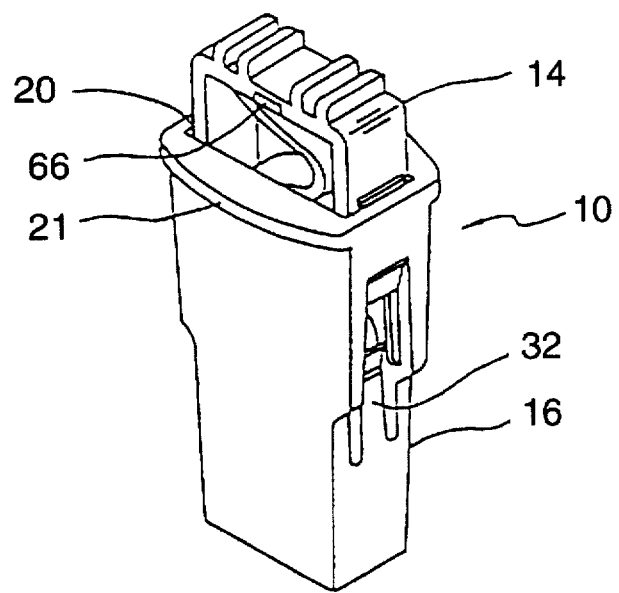
FIG. 1 schematically shows a perspective view of a lancet assembly 10 before use in which a lancet structure 14 is incorporated into a holder 16.
Figure 21:
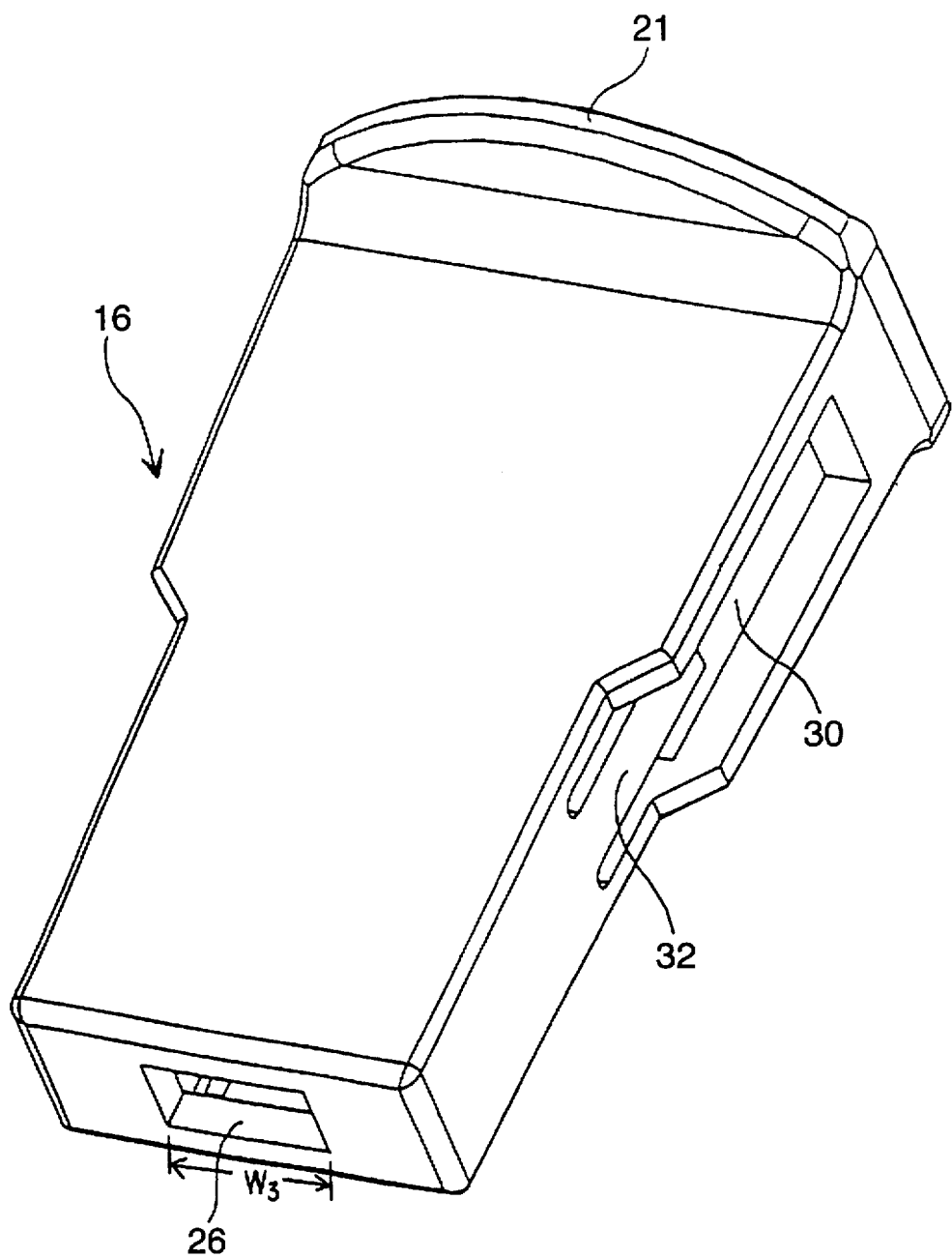
FIG. 21 shows a perspective view of a holder which may be used for the lancet assembly according to the present invention.

In any embodiment according to the present invention described above, the holder 16 used for the lancet structure may be substantially the same as the holder 16 shown in FIG. 1, which holder is shown alone in FIG. 21.

In any embodiment of the present invention described above, the ejector preferably has an entanglement preventive means. The means is a member which protrudes from the arms and/or the base portion of the ejector inwardly therefrom, and the means of a certain ejector functions to prevent the arms of other ejector and/or the arms of other lancet body from entering the inside space of said certain ejector and entangling with arms of said certain ejector, namely the means prevent a plurality of the ejectors and/or the lancet bodies from being in an interlocked condition. The entanglement preventive means is, for example, in the form of a flap portion 120 which protrudes from the arms 60 of the ejector 42 toward inside thereof, as shown in FIG. 11. In the shown embodiment, the entanglement preventive means 120 includes a wave-shaped portion which corresponds to the wave-shaped portion of the spring member 54 and which is separated from the spring member 54 by a clearance so as not to interrupt the compression of the spring member 54. Such entanglement preventive means close the space inside the ejector 42 as much as possible, and its shape is not particularly limited. However, it has a portion of which shape is similar to the spring member 54. Any other shape may be possible provided that the means prevent the entanglement.

Figure 22:
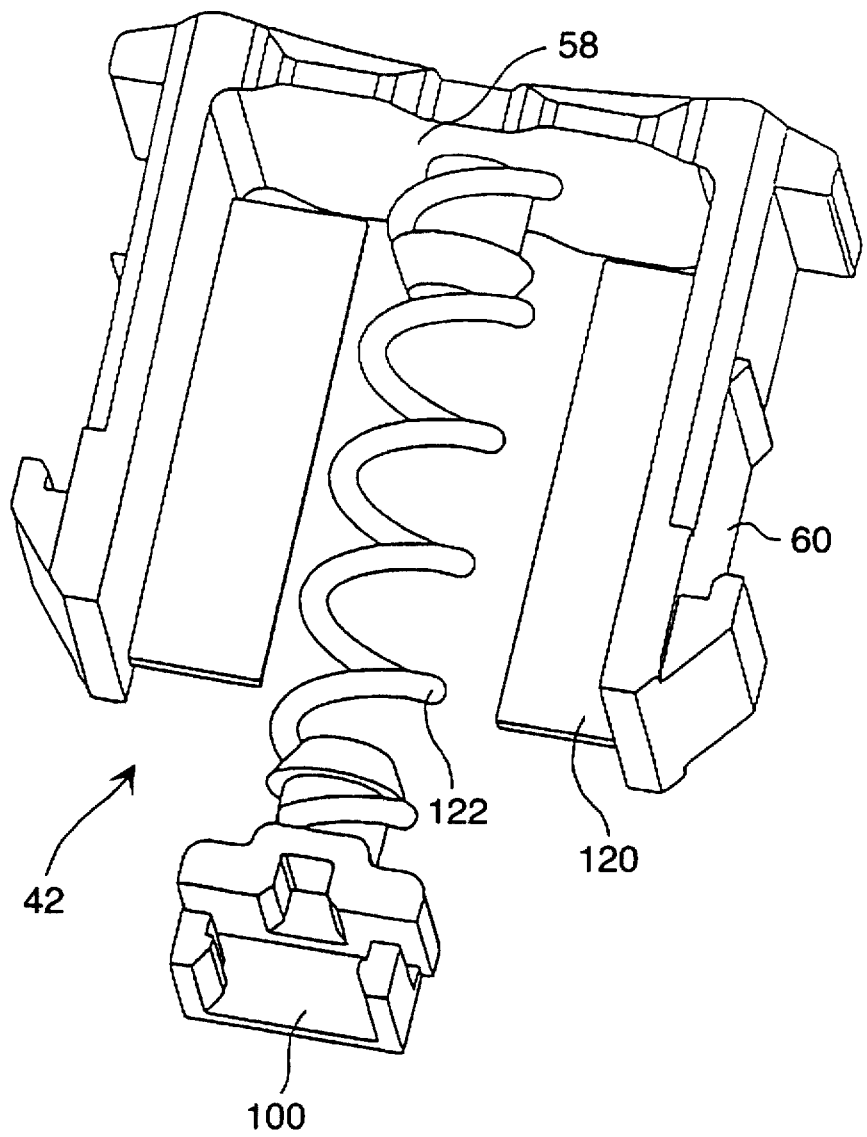
FIG. 22 schematically shows a perspective view of another ejector which may be used for the lancet assembly according to the present invention.
Figure 23:
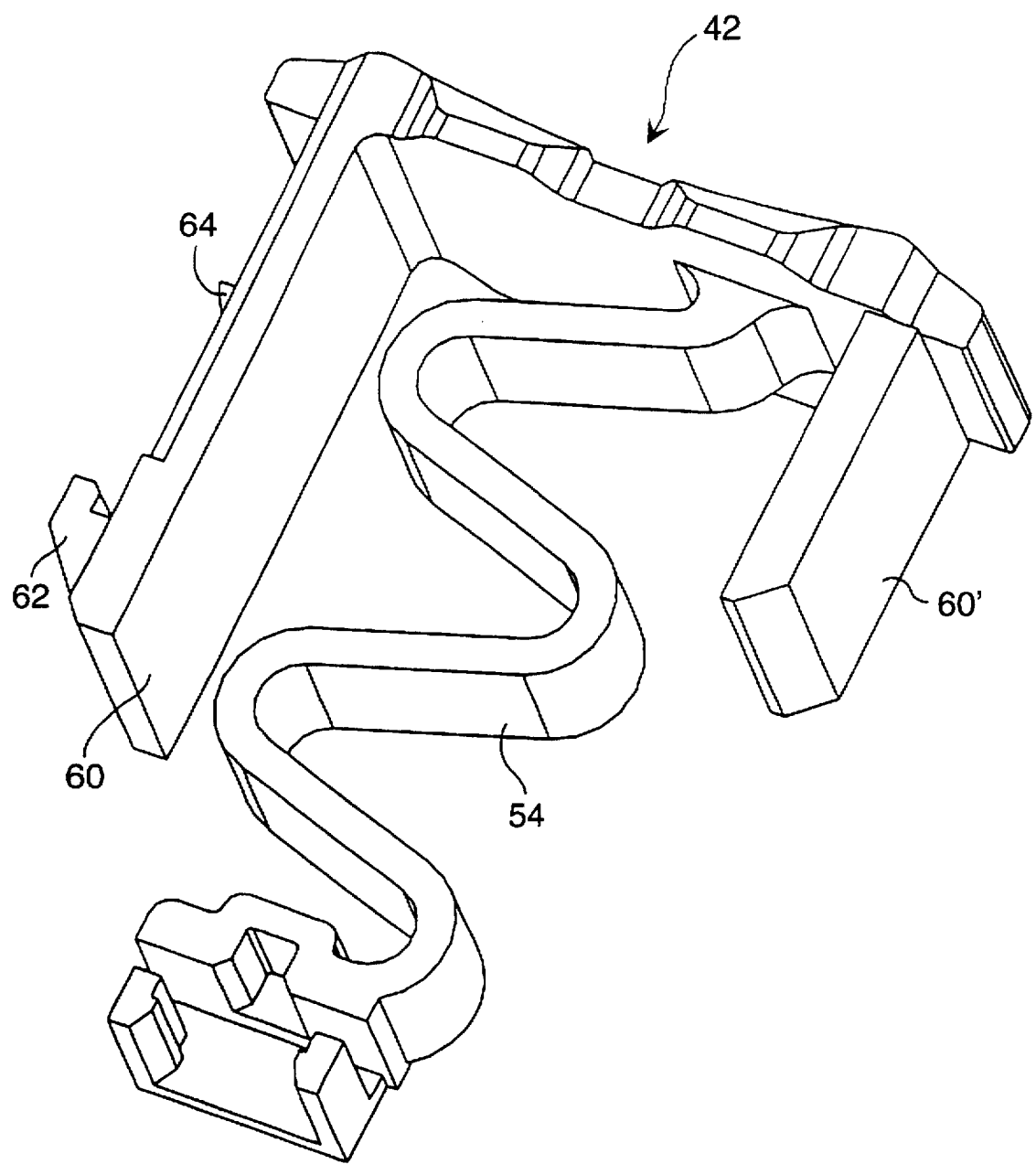
FIG. 23 schematically shows a perspective view of a further ejector which may be used for the lancet assembly according to the present invention.

In the embodiments according to the present invention described above, the ejecting means is composed a unitary member of the arms, the base portion and the spring means, although the spring means may be replaced with a spring in the form of a coil, which embodiment is shown in FIG. 22. In the embodiment shown in FIG. 22, the spring 122 is connected to the base portion 58 with any proper means, and the spring comprised a female member 100 at the other end, which is connected to the lancet body. The embodiment shown in FIG. 22 has an entanglement preventive means 120 is in the form of a rectangular flap which protrudes toward the coil spring.

In the embodiments according to the present invention described above, the holder 16 and the lancet structure 14 (excluding the spring member) is of a symmetrical shape in an upper half and the lower half respect to, for example, the center line (X—X') in FIG. 9. However, they are not necessarily of the symmetrical shape. For example, at least the upper or lower half having the engagement, the stop and the ejection treatments with the presence of the spring member 54 can operate as the lancet assembly 10 as described above. An ejector 42, a lancet member 40 and a holder 16 of such embodiment are shown in FIGS. 23 to 26.

Figure 24:
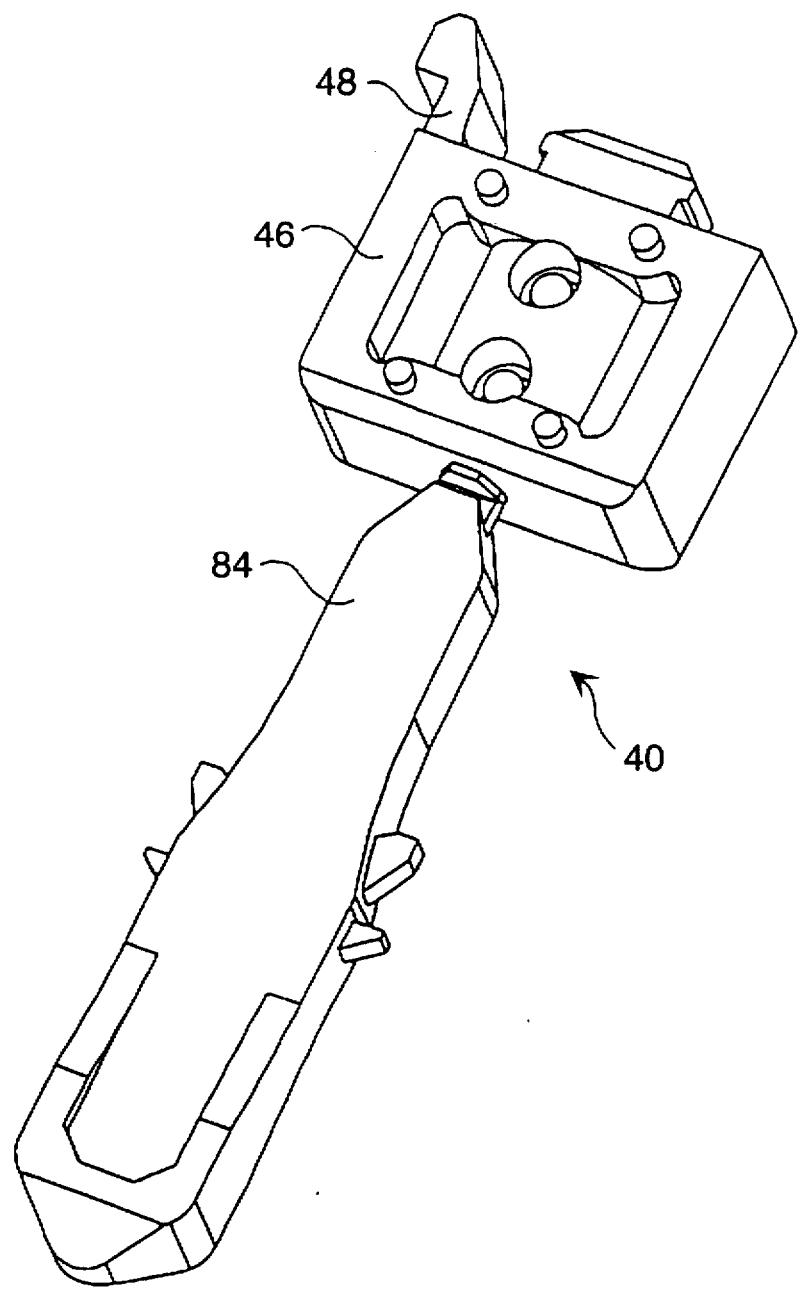
FIG. 24 schematically shows a perspective view of another lancet member which may be used for the lancet assembly according to the present invention.
Figure 25:
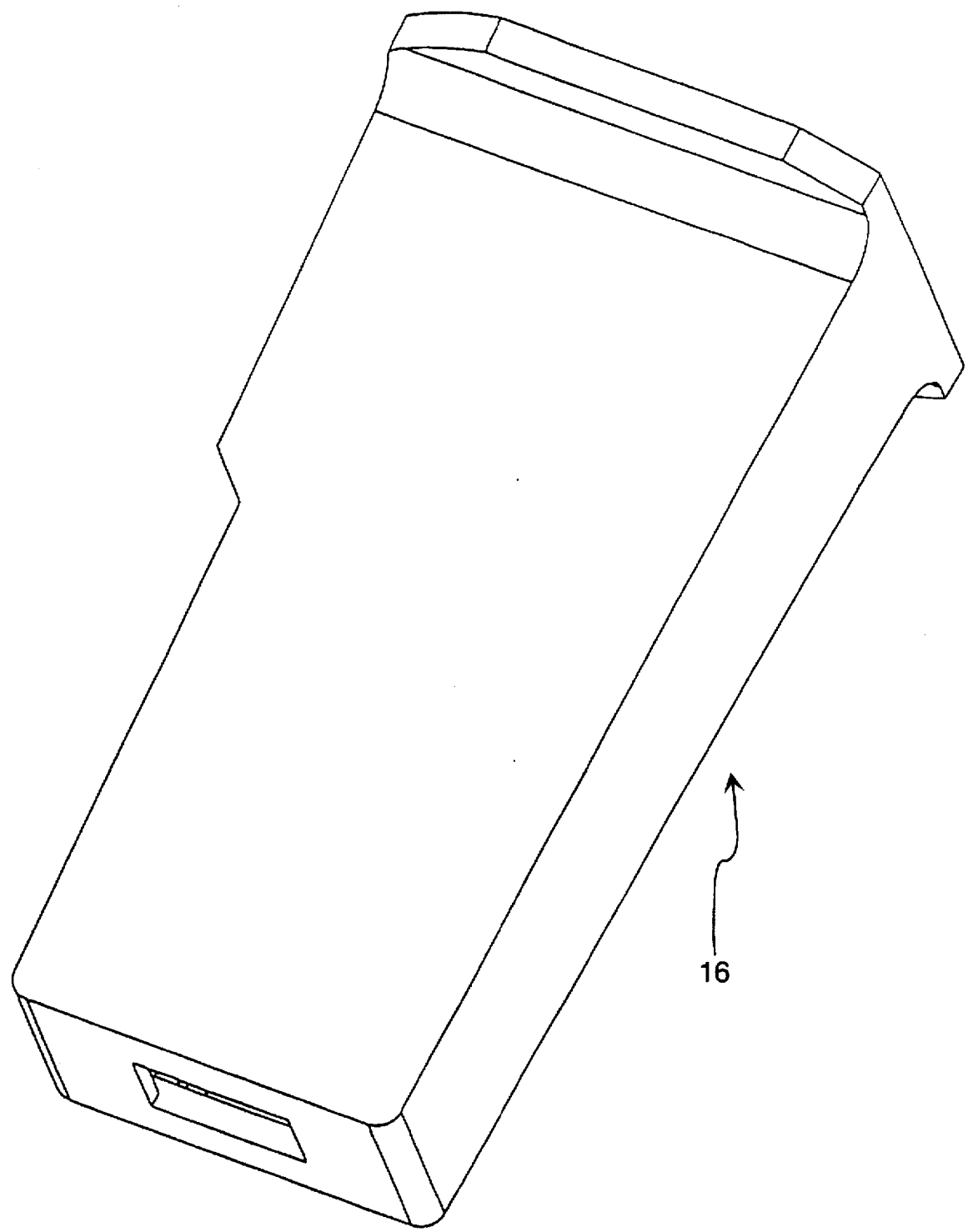
FIG. 25 schematically shows a perspective view of another holder which may be used for the lancet assembly according to the present invention.

As seen from those drawings, the lancet assembly of such embodiment can be composed of an ejector including a single arm 60 having lips 62 and 64 and a single arm 60' without a lip (as shown, for example, in FIG. 23) and a lancet member 40 including a lancet body 46 which has a single arm 48 (as shown, for example, in FIG. 24). In such embodiment, the holder 16 may comprises a single channel on one side as shown in FIG. 25, which corresponds to those members 42 and 40.

Figure 26:
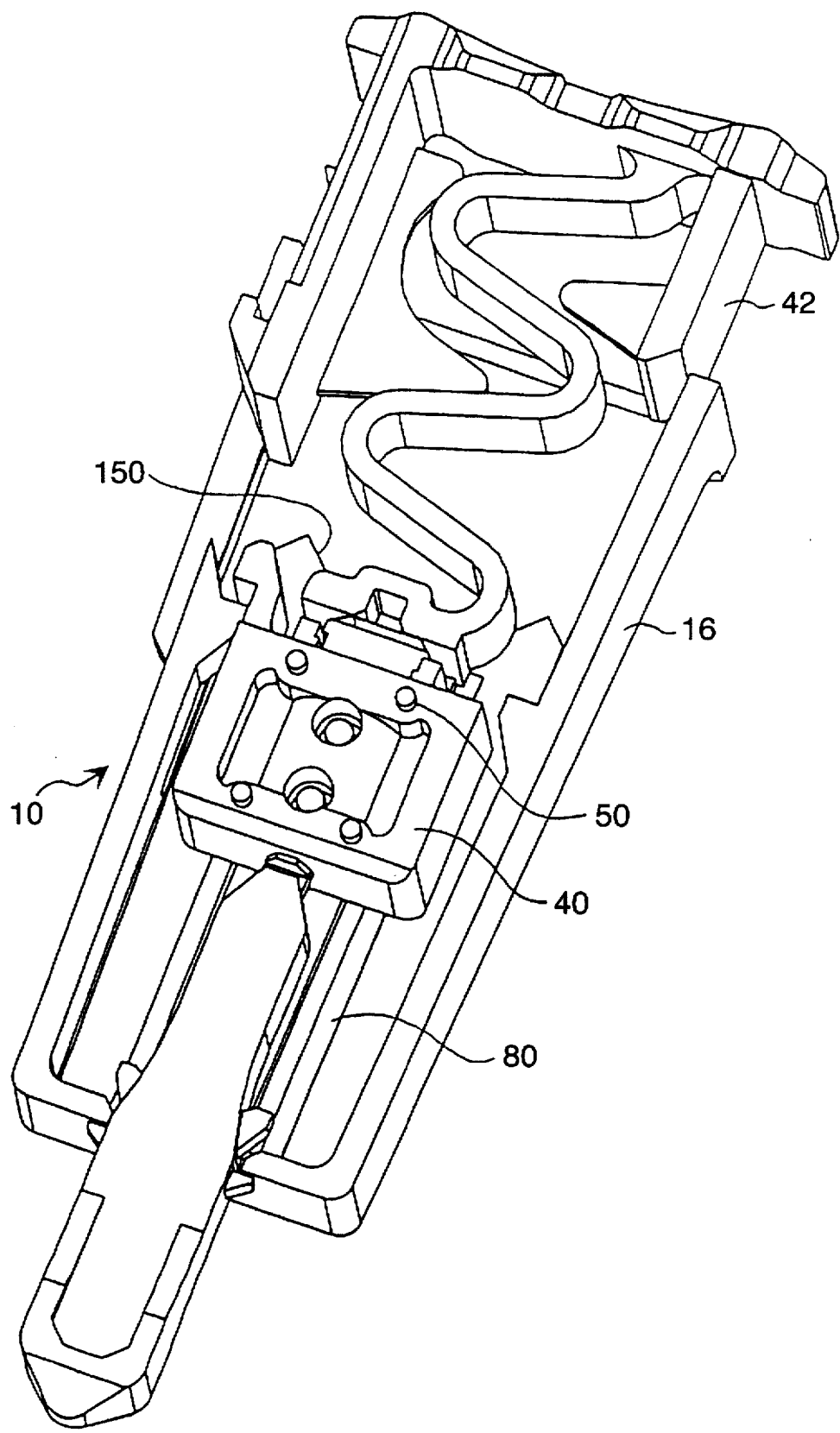
FIG. 26 schematically shows a perspective view of a lancet assembly produced by assembling the members shown in FIGS. 23 to 25 in which an upper half portion of the holder is cut away so as to easily understand a position inside the holder.

FIG. 26 shows a perspective view of the lancet assembly 10 according to the present invention formed by the combination of the ejector 42, the lancet member 40 and the holder 16. In FIG. 26, upper half of the holder is cut away so as to understand a position of the ejector and the lancet member.

FIG. 27A and 27B schematically shows an assembling method of the lancet assembly of the present invention, in which the lancet assembly of the third embodiment is shown in the perspective views in combination of side views from the right ends thereof (when observed from the right end of the perspective view). The ejectors 42 are aligned and adjacent to one another along the line 144 while they are sandwiched by the assembling tools 132 and 134. The lancet members 40 are aligned and separated by a predetermined space along the line 146 while they are sandwiched by the assembling tools 136 and 138. The holders 16 are aligned and adjacent to one another along the line 148 while they are sandwiched by the assembling tools 140 and 142. Each assembling tool of the front side are shown cut away so as to understand inside positions.

As seen from FIG. 27A and 27B, the ejector 42 is supported by the tools 132 and 134 while its ribs 130 are located within channels 152, spacer members 128 function to separate the ejector itself by a predetermined space (in an adjoining condition of the spacer members 128) so that separation pitch of the ejector corresponds to that of the holder 16 aligned along the lower line 148. A separation pitch of the middle line 146 has been changed beforehand so that it correspond to the pitch of the holder 16 along the lower line 148 as in the lancet member 146. In view of the presence of the spacer members 128 as described above, merely positioning of the ejectors 42 in the adjoining condition is sufficient, to align the ejectors 42 with the lancet members 40. Accordingly, it is unnecessary to change the separation pitch required along the line 146 of the lancet members 40.

Starting from the shown position, the lancet members 40 are first dropped down into the holders 16 by opening the tools 126 and 138 of the line 146. Then, the line 144 is lowered toward the line 148 so that it depresses the ejectors 42 into the holders 16, whereby the lancet assemblies according to the present invention are formed with snap fitting of the ejectors 42 and the lancet members 40.

In the second aspect, the present invention provides various parts for the formation of the lancet assemblies described above, for example, the lancet member, the covered pricking member, the lancet structure, the ejector and the holder. Explanations described above are referred to for detailed descriptions of those parts.

EXAMPLES

Example 1

Metal molds for the holder (to mold one piece), metal molds for the lancet member and the ejector (to mold one piece) and metal molds for the covered pricking member 84 (to mold eight pieces), namely, the metal molds for molding substantially the same members as those in FIGS. 16 and 10 were fabricated, and all the members molded by the metal molds were substantially the same as the holder and lancet structure shown in FIGS. 16 and 10.

The lancet structure was so arranged that the covered pricking member was press fit to the lancet structure (see FIG. 10).

As to the materials used, an ABS resin (Toyorac #500, commercially available from Toray Industries, Inc.) was selected for the holder 16, a polyacetal resin (of a copolymer type) (Tenac #4520, commercially available from Asahi Chemical Industry Co., Ltd.) was selected for the lancet member and the ejector (40 and 42.) and a linear low density polyethylene resin (#AJ 5380, commercially available from Mitsui-Nisseki Polymer Co., Ltd.) was selected for the covered pricking member 84.

For the blade, stainless steel 440 A (commercially available from Hitachi Metals, Ltd., 0.16 mm thickness) was selected. A transferring mold and a stamping out mold (for one piece) were fabricated and blades each having a predetermined shape (not separated and connected to a carrier) were produced using a pressing machine (ten-ton type). An edge portion of the blade was then ground and abraded by means of a blade grinder.

The metal molds for the holder were installed on to a horizontal injection molder (forty-ton type, commercially available from Nissei Plastic Industrial Co., Ltd.), and the holders were produced using the ABS resin. The metal molds for the lancet member and the ejector were similarly installed, and the lancet members and the ejectors were produced using the acetal resin.

Then, the metal molds for the resin covered pricking member were installed onto a vertical injection molder (thirty-ton type, commercially available from Nissei Plastic Industrial Co., Ltd.), and the blades (eight pieces) connected to the carrier were inserted into the molds, so that the resin covered pricking members were obtained using the PE resin. After the molding, notches having a depth of 0.3 to 0.35 mm were provided onto both sides of portions near the connection of a convex engaging portion of the resin covered pricking member to the sheath member with a tool containing a razor blade (the notch did not reach the pricking member). Then, the resin covered pricking members were separated from the carrier to have individual pieces.

One hundred of the holders 16, the lancet members 40 and the ejectors 42 and the resin covered pricking members 84 each were thus produced.

The above molding processes were conventional injection molding ones and no specific technique was required.

Firstly, the resin covered pricking member 84 was connected to the lancet body 46 by means of press fitting using a bench pressing machine to form the lancet structure 14. The lancet connected structure was then inserted into the holder 16 through the opening 20 by inserting such that a tip portion 98 of the resin covered pricking member 84 was in the holder 16 first. The insertion itself was smoothly carried out since a cut away portion was formed at the tip 98 of the resin covered pricking member for easy reception (for example, as shown in FIG. 10) and guiding channels 80 were formed inside the holder so as to guide the lancet structure (thus, the lancet structure is automatically controlled to have a predetermined orientation and attitude).

In the examples, as the lancet structure 14 proceeded ahead inside the holder, the first stops 92 of the resin covered pricking member 84 contacted the end wall 96 of the holder having the aperture 26. Although the width of the first stops is larger than that of the aperture, the first stops easily passed through the aperture 26 since the resin of the stops was the PE and the tapers for the easy reception were provided to the stops. Then, the arms 48 of the lancet structure abutted against the engaging protrusions 34 provided along the side surfaces of the holder, and stopped proceeding. In this position, the second stops 94 were not exposed from the end surface 96 of the holder, but were held in the predetermined position in the holder (as shown in FIG. 19).

In such a position, the inventor tried to force the resin covered pricking member 84 into the holder 16, and confirmed that it was impossible to do so since the first stops 92 had the irreversible shape which does not allow retraction into the holder 16. Thus, the first stops 92 function as explained above.

Next, in order to have the lancet to be ready to use, the holder 16 was held by the left hand and tip portion 98 of the resin covered pricking member was pinched using two fingers of the right hand, and then the tip portion 98 was pulled. The entire resin cover 82 was pulled out of the holder 16 with a feeling of the second stops 94 passing through the aperture 26. The resin cover 82 was broken at the notch as predetermined. (The lancet body of the lancet structure 14 did not move when the resin cover 82 was removed since it was held by engagement of the protrusions 34 with the arms 48).

Thereafter, when the lancet structure 14 was further depressed into the holder 16, the engagement condition was released so that the lancet member 40 (including the blade) was ejected. This ejection process was recorded using an ultra-high speed VCR (video tape recorder) and then the ejection was checked by playing back the video tape. Thus, it has been confirmed that the blade was properly exposed through the aperture 26 to the outside and then properly returned into the inside of the holder.

The samples used in the above examples had the following sizes:

Resin cover thickness (at notch): 1.5 mm
Resin cover width (at notch): 2.5 mm
Notch depth (each of the both sides): 0.3 to 0.35 mm
Holder aperture (26): width ($W_3$) 4.7 mm×height 3.1 mm
Holder inside height: 4.3 mm
Width of first stops ($W_1$): 4.9 mm
Width of second stops ($W_2$): 5.4 mm Then, the inventor tried to twist the resin cover 82 without drawing. However, it could not be twisted since the second stops 94 had a larger width than that of the inside height of the holder.

Example 2

In order to produce the lancet assembly of the third embodiment of the first aspect according to the present invention (substantially the same assembly shown in FIG. 15), metal molds for the holder 16 (to mold one piece), metal molds for the ejector 42 (to mold one piece) and metal mold for the lancet member 40 (the pricking member is in the form of a blade) were formed.

As to the material used, a transparent ABS resin (#920, commercially available from Toyay Industries, Inc.) was selected for the holder 16 so as to observe connection and operation of the ejector 42 and the lancet member 40 therein, a polyacetal resin (Tenac #4520, commercially available from Asahi Chemical Industry Co., Ltd.) was selected for the ejector 42, and a linear low density polyethylene resin (#AX 6820, commercially available from Mitsui-Nissei Polymer Co., Ltd.) was selected for the lancet member. The pricking member was of a blade type and its material was the same as that of Example 1 (stainless steel 440 A, commercially available from Hitachi Metals, Ltd., 0.16 mm thickness).

The length (along the ejection direction) of the holder 16 was longer by 1.5 mm than that of Example 1 (the second embodiment of the first aspect) since snap fitting members (namely, the fitting members 100 and 102) were provided on the spring member 54 and the lancet member 40.

One hundred of the holders, the ejectors and lancet members (including the inserted pricking members) each were produced using the same molders as in Example 1. Molding was carried out without any problem.

One hundred of the ejector were charged into a vibrating bowl feeder (commercially available from NTN Co., Ltd.) then the feeder was operated for 30 minutes, followed by entanglement observation of the ejectors. No entanglement was observed, which has confirmed that the flaps 120 are effective for prevention of the entanglement.

Based on the above results, it has been confirmed that supplying ejectors 42 to a liner feeder as shown in FIG. 27A and 27B using the vibrating bowl feeder so as to automatically assemble the lancet assemblies.

Then, assembling of the lancet assembly was tested. In order to facilitate the automatic assembling as shown in FIG. 27A and 27B, a small handpress was prepared and it was arranged to form a simple tool which can support the holder 16 perpendicularly. The tool was so equipped on a handpress table that there is provided a space 154 from a table surface to the holder end so that no problem occurs when a tip portion 98 of the covered pricking member of the lancet member was exposed from through the aperture 26 of the holder bottom. One side of the tool was cut away to observe almost all of one side of the supported holder.

The lancet member 40 was dropped above the holder opening 20 with aligning the axes of the holder and the lancet member (spontaneous dropping). The lancet member 40 was lead to the guide 150 (namely, the pins 50 shown in FIG. 26 were guided by the channels 80) and so stopped that the first stops 92 of the covered pricking member 82 abut against the lower aperture 26. In this position, the lancet member 40 was held in such attitude that the axis of the holder was aligned with the axis of the lancet member since the lancet member 40 was guided with the guiding channels 80 with the projecting portions (pins 50) provided on the member.

Then, a tool was produced which can support an upper portion of the ejector 48 using the ribs 130 provided on the base portion 58, and the ejector was charged on the tool, which was placed on the arms of the handpress. When the tool containing the ejector was gradually lowered, the female member 100 at the lower end of the ejector contacts with the male member 102 which was provided on the upper portion of the lancet member. When the tool supporting the ejector was further lowered, the spring member 54 was compressed and the lancet member 40 was depressed downward due to repelling force from the compression, resulting in that the first stops 92 on the covered pricking member 82 passed through the aperture 26, whereby the lancet member was engaged with the engaging protrusion 34 and stopped. Subsequently to stopping, snap fitting of the spring member 54 of the ejector with the lancet member was automatically completed.

The above movements in the holder were observed fully and precisely through a transparent wall of the holder.

Twenty of the lancet assembly was produced, all of which were smoothly assembled. Only the opening of the female member of the ejector had the front and the back surfaces, and assembling of the twenty assemblies were carried out without a problem regardless of the front and the back surfaces.

(Ejection Test)

Using the twenty lancet assemblies thus assembled, ejection tests were carried out. First, the covered member 82 protruding from the holder aperture was pulled out. Placing the holder aperture against a silicone rubber sheet having a thickness of 3 mm, and then the ejector was depressed. The lancet member was ejected with released from its engagement position and retracted inside the holder automatically. All of the twenty lancet member was returned into the holder. Upon checking them, no ejector was disconnected from the lancet member.

Practical applicability of the lancet assembly of the third embodiment of the first aspect has been confirmed based on the above tests.

I claim:

1. A lancet assembly including an ejector assembly, the ejector assembly comprising:

a base member;

a spring member coupled to the base member and extending therefrom; and at least one flap extending from the base member toward the spring member substantially adjacent the spring member, the flap being separated from the spring member by a gap, said flap acting as an entanglement preventative means whereby said flap substantially prevents foreign objects from becoming entangled with the spring member during handling of the ejector assembly before assembly of the ejector assembly into the lancet assembly.

2. The lancet assembly of claim 1 wherein the base member includes:

a base portion to which said spring member is coupled; and at least one arm extending upwardly from the base portion substantially parallel the spring member;

wherein the spring member is generally in the form of a wave, and wherein at least one flap has a waved edge disposed substantially adjacent the spring member such that the waved edge of the flap generally follows the waved form of the spring member.

3. The lancet assembly of claim 2 wherein the flap is integrally formed with the arm.

4. The lancet assembly of claim 1 wherein the base member is a U-shaped structure which includes:

a base portion; and two arms upwardly extending from the base portion substantially parallel to and disposed along opposite sides of the spring member;

wherein the spring member has a generally wave-like contour, and wherein the at least one flap has a waved edge disposed between one of said arms and said spring member substantially adjacent the spring member such that the waved edge of the flap generally follows the wave-like contour of the spring member.

5. The lancet assembly of claim 1 wherein the base member includes:

a base portion; and at least one arm extending upwardly from the base portion substantially parallel the spring member;

wherein the spring member is in the form of a coil, and the at least one flap has a substantially straight edge disposed substantially adjacent the spring member.

6. The lancet assembly of claim 5 wherein the flap is integrally formed with the arm.

7. A lancet assembly including a lancet structure and a holder for at least partially enclosing the lancet structure, the lancet structure comprising:

a lancet member;

a blade coupled to the lancet member;

an ejector operable to move the lancet member relative to the holder to extend the blade from the holder in an ejection direction;

a molded resin cover covering an exposed portion of the blade; and a notch in the resin cover at a position at which the resin cover is breakable to expose the exposed portion of the blade when the resin cover is pulled in the ejection direction, the notch being of a depth such that it does not interfere with the sterility of the blade.

8. The lancet assembly of claim 7 wherein the notch is molded.

9. The lancet assembly of claim 8 wherein the notch is further cut into the cover after the resin cover is molded.

10. The lancet assembly of claim 7 wherein the notch is cut into the cover after the resin cover is molded.

11. The lancet assembly of claim 7 wherein said notch is narrow slit.

12. A method for assembling a lancet assembly having a lancet structure and a holder having a cavity, the lancet structure including an ejector, a lancet body, a sterile pricking member and a cover over the pricking member, the lancet assembly having an ejection axis along which the pricking member is ejected through the holder during use, said method comprising the steps of: holding the holder, inserting the lancet structure into the holder substantially along the ejection axis such that a portion of the cover over the sterile pricking member extends partially through an ejection opening in a wall of the holder.

13. The method as claimed in claim 12 wherein the ejector, lancet body, and cover over the pricking member are formed as a unitary lancet structure and the step of inserting the lancet structure includes inserting the unitary lancet structure into the holder.

14. The method as claimed in claim 12 further including the step of coupling the covered pricking member to the lancet body.

15. The method as claimed in claim 14 wherein the coupling step includes sliding a male portion of the covered pricking member into a female portion of the lancet body in a direction substantially perpendicular to the ejection axis prior to the step of inserting the lancet structure into the holder.

16. The method as claimed in claim 14 wherein the step of inserting the lancet structure includes the steps of inserting the coupled lancet body and covered pricking member into the holder in the direction of the ejection axis, inserting the ejector into the holder, and coupling the ejector to the lancet body.

17. The method as claimed in claim 12 wherein the lancet body and the covered pricking member are formed as a unitary lancet member, and the step of inserting the lancet structure includes the steps of inserting the unitary lancet member into the holder in the direction of the ejection axis, inserting the ejector into the holder, and coupling the ejector to the lancet body.

18. The method as claimed in claim 12 wherein the step of holding the holder comprises substantially sandwiching the holder within a first assembly tool, the method further comprising the steps of substantially sandwiching the lancet structure within a second assembly tool, aligning the lancet structure with the holder, and releasing the lancet structure from the second assembly tool to insert the lancet structure into the holder.

19. The method as claimed in claim 18 wherein the step of sandwiching the lancet structure includes the step of sandwiching the lancet structure between first and second halves of the second assembly tool, and the step of releasing the lancet structure includes the step of separating the first and second halves of the second assembly tool.

20. The method as claimed in claim 12 wherein the step of holding the holder comprises substantially sandwiching the holder within a first assembly tool, the method further comprising the steps of substantially sandwiching the lancet body and covered pricking member within a second assembly tool, substantially sandwiching the ejector within a third assembly tool, aligning the lancet body and covered pricking member with the holder, and releasing the lancer body and covered pricking member from the second assembly tool to insert the lancet body and covered pricking member into the holder, aligning the ejector with the lancet body, covered pricking member, and holder, and releasing the ejector from the third assembly tool.

21. The method as claimed in claim 20 wherein the step of sandwiching the lancet holder and covered pricking member includes the step of sandwiching the lancet body and covered pricking member between first and second halves of the second assembly tool, and the step of releasing the lancet body and covered pricking member includes the step of separating the first and second halves of the second assembly tool.

22. The method as claimed in claim 20 wherein the step of sandwiching the ejector includes the step of sandwiching the ejector between first and second halves of the third assembly tool, and the step of releasing the ejector includes the step of separating the first and second halves of the third assembly tool.

23. The method as claimed in claim 21 wherein the step of sandwiching the ejector includes the step of sandwiching the ejector between first and second halves of the third assembly tool, and the step of releasing the ejector includes the step of separating the first and second halves of the third assembly tool.

24. The method as claimed in claim 18 further comprising the steps of automatically feeding the holder to the first assembly tool and automatically feeding the lancet assembly to the second tool.

25. The method as claimed in claim 20 further comprising the steps of automatically feeding the holder to the first assembly tool and automatically feeding the lancet assembly to the second tool.

* * * * *

UNITED STATES PATENT AND TRADEMARK OFFICE
CERTIFICATE OF CORRECTION

PATENT NO. : 5,755,733
DATED : May 26, 1998
INVENTOR(S) : MORITA

It is certified that error appears in the above-identified patent and that said Letters Patent is hereby corrected as shown below:

ON THE TITLE PAGE:
Page 2, column 2, line 1 of References Cited: "IngaLz" should read -- Ingalz --.

Column 11, line 7: "(machine" should read --machine(--.
Column 12, line 37: "fitting. Such" should read --fitting, such--.
Column 12, line 39: "to performing of" should read --performing of--.
Column 13, line 54: "difficult." should read --difficulty.--.
Column 21, line 16: "member 146" should read --member line 146--.
Column 21, line 56: "42,)" should read --42),--.
Column 24, lines 13 and 14: "150 (namely, the pins 50 shown in FIG.26 were" should read --150 shown in Fig.26 (namely, the pins 50 were--.

In Claim 20, Column 27, line 3: "lancer" should read --lancet--.

Signed and Sealed this

Third Day of November, 1998

*Attest:*

*Attesting Officer*

BRUCE LEHMAN
Commissioner of Patents and Trademarks